United States Patent
An et al.

(10) Patent No.: US 10,684,339 B2
(45) Date of Patent: Jun. 16, 2020

(54) DUAL FLIP ANGLE MULTI-ECHO ULTRA-SHORT ECHO TIME (DUFA-MUTE) MAGNETIC RESONANCE IMAGING (MRI) SYSTEMS AND METHODS

(71) Applicant: Washington University, St. Louis, MO (US)

(72) Inventors: Hongyu An, St. Louis, MO (US); Meher Juttukonda, Nashville, TN (US); Cihat Eldeniz, St. Louis, MO (US); Yasheng Chen, St. Louis, MO (US)

(73) Assignee: WASHINGTON UNIVERSITY, St. Louis, MO (US)

( * ) Notice: Subject to any disclaimer, the term of this patent is extended or adjusted under 35 U.S.C. 154(b) by 264 days.

(21) Appl. No.: 15/872,407

(22) Filed: Jan. 16, 2018

(65) Prior Publication Data

US 2018/0203084 A1 Jul. 19, 2018

Related U.S. Application Data

(60) Provisional application No. 62/445,817, filed on Jan. 13, 2017.

(51) Int. Cl.
*G06K 9/00* (2006.01)
*G01R 33/56* (2006.01)
(Continued)

(52) U.S. Cl.
CPC ........ *G01R 33/5608* (2013.01); *A61B 5/0035* (2013.01); *A61B 5/055* (2013.01);
(Continued)

(58) Field of Classification Search
CPC .......... A61B 5/0035; A61B 5/055; A61N 2005/1055; A61N 5/1039; G01R 33/4812;
(Continued)

(56) References Cited

U.S. PATENT DOCUMENTS 8,655,038 B2 2/2014 Keereman et al.
2012/0076378 A1* 3/2012 Keereman .......... G01R 33/4808
382/131

(Continued)

FOREIGN PATENT DOCUMENTS

WO 2015103184 A1 7/2015

OTHER PUBLICATIONS

Johansson, Adam, et al. "Voxel-wise uncertainty in CT substitute derived from MRI." Medical physics 39.6Part1 (2012): 3283-3290. (Year: 2012).*

(Continued)

*Primary Examiner* — Avinash Yentrapati
(74) *Attorney, Agent, or Firm* — Armstrong Teasdale LLP

(57) ABSTRACT

Systems and methods for producing pseudo-CT images using a dual flip angle multi-echo ultra-short echo time (DUFA-MUTE) MRI method are disclosed. The DUFA-MUTE MRI imaging method includes obtaining MR signals according to a DUFA-MUTE MRI sequence that includes first and second multiple ultrashort echo time (MUTE) sequence characterized by first and second flip angles FA1/FA2, and in which both MUTE sequences obtain MR signals at first and second echo times TE1/TE2. HU values are assigned to each imaged voxel based on each voxel's R1 value calculated from the MR signals, as well as each voxel's assigned tissue type. The imaged voxels and assigned HU values are combined to produce a pseudo-CT image. Pseudo-CT images optionally form the basis for attenuation maps suitable for use in combined PET/MRI systems and/or electron density maps suitable for use in radiation therapy systems.

24 Claims, 21 Drawing Sheets
(1 of 21 Drawing Sheet(s) Filed in Color)

(51) Int. Cl.
  *A61B 5/00* (2006.01)
  *A61B 5/055* (2006.01)
  *G01R 33/48* (2006.01)
  *A61N 5/10* (2006.01)
(52) U.S. Cl.
  CPC ..... *G01R 33/4812* (2013.01); *G01R 33/4816* (2013.01); *A61N 5/1039* (2013.01); *A61N 2005/1055* (2013.01); *G06T 2207/10081* (2013.01); *G06T 2207/10088* (2013.01)
(58) Field of Classification Search
  CPC ............ G01R 33/4816; G01R 33/5608; G06T 2207/10081; G06T 2207/10088
  See application file for complete search history.

(56) References Cited

U.S. PATENT DOCUMENTS

| | | | | |
|---|---|---|---|---|
| 2016/0066874 A1* | 3/2016 | Huang | ................. | A61B 6/5258 600/411 |
| 2016/0310761 A1* | 10/2016 | Li | ..................... | A61N 5/1038 |
| 2019/0015060 A1* | 1/2019 | Weiss | ................. | A61B 6/5294 |

OTHER PUBLICATIONS

Johansson, Adam, Mikael Karlsson, and Tufve Nyholm. "CR substitute derived from MRI sequences with ultrashort echo time." Medical physics 38.5 (2011): 2708-2714. (Year: 2011).*
Berker, Yannick, et al. "MRI-based attenuation correction for hybrid PET/MRI systems: a 4-class tissue segmentation technique using a combined ultrashort-echo-time/Dixon MRI sequence." Journal of nuclear medicine 53.5 (2012): 796-804. (Year: 2012).*
Guerini, H. et al., "Fat Suppression with Dixon Techniques in Musculoskeletal Magnetic Resonance Imaging: A Pictorial Review," Semin Musculoskelet Radiol, 19(4): 335-347 (2015).
Juttukonda, M.R. et al., "MR-Based Attenuation Correction for PET/MRI Neurological Studies with Continuous-Valued Attenuation Coefficients for Bone Through a Conversion from R2 to CT-Hounsfield Units," Neuroimage 112: 160-168 (2015).
Ma, J., "Dixon Techniques for Water and Fat Imaging," Journal of Magnetic Resonance Imaging, 28(3): 543-558 (2008).
Wagenknecht, G. et al., "MRI for Attenuation Correction in PET: Methods and Challenges," Magnetic Resonance Materials in Physics, Biology & Medicine, 26(1): 99-113 (2013).

* cited by examiner

DUAL FLIP ANGLE MULTI-ECHO ULTRA-SHORT ECHO TIME (DUFA-MUTE) MAGNETIC RESONANCE IMAGING (MRI) SYSTEMS AND METHODS

CROSS-REFERENCE TO RELATED APPLICATION

This application claims the benefit of U.S. Provisional Application No. 62/445,817 filed Jan. 13, 2017, which is incorporated herein in its entirety.

STATEMENT REGARDING FEDERALLY SPONSORED RESEARCH & DEVELOPMENT

This invention was made with government support under Grant No. 1R01NS082561 awarded by the National Institutes of Health. The government has certain rights in the invention.

BACKGROUND

The benefits of superior soft tissue contrast and versatility of MR imaging in providing anatomic, metabolic and physiological information has made MRI an important medical imaging tool for a variety of conditions, including the diagnosis of cancer and other soft tissue-related disorders. However, because MR imaging measures parameters such as proton density and MR relaxation rates, bone appears invisible in conventional MR images due to the low spin density and rapid relaxation associated with bone. For the visualization of bone tissue, additional medical imaging methods, such as CT imaging, are typically used.

Registration of the MR and CT images is typically used to produce a combined MR/CT image that includes both bone and soft tissues, but the process of registration is challenging because there are relatively view anatomical features visible in both MR images and CT images to serve as reference positions. As described above, MR images typically feature the distribution of various soft tissues but do not include bone, whereas CT images typically feature the distribution of bone but do not include various soft tissues.

At least several methods have been proposed to produce pseudo-CT images, defined herein as images that include a map of Hounsfield Units (HU) estimated from measured MR parameters obtained by an MR scanner. The pseudo-CT images include representations of soft tissues and bones derived from the same set of measured MR parameters, and therefore ameliorate any artifacts introduced by registration of multiple images obtained MR using separate devices. Further, the pseudo-CT images provide high-quality images of bones and attached soft tissues such as tendons, ligaments, and muscles without exposing the patient to potentially harmful radiation.

Atlas-based approaches typically rely on precompiled atlases of paired MR and CT images in combination with an algorithm to generate pseudo-CT images from the patient MR images. However, the atlas-based approaches are prone to errors for the imaging of patients falling outside of the anatomy represented by the population data used to compile the atlases. Direct MR imaging methods typically make use of MR signals obtained using specialized MRI data acquisition sequences, such as Dixon MRI sequences, ultra-short echo time (UTE) MRI sequences, or zero echo time (ZTE) MRI sequences to segment the resulting MR images into several tissue classes, but the challenge remains to determine the distribution of tissue densities within each segmented region based on MR signals alone. Additional direct MR imaging methods similarly perform UTE or ZTE MR imaging for tissue segmentation and further make use of a pre-calibrated conversion of an MR-derived quantity, such as DUTE $R2^*$ or the inverse logarithm of the ZTE signal, to determine a CT HU for the bone tissue. These additional direct MR imaging methods typically use MR-to-CT conversion relationships derived from population data, resulting in enhanced speed over previous atlas-based methods and better accounting for variations between individual subjects. However, the MR-to-CT conversion relationships used in these additional direct MR imaging methods potentially vary due to variations in measured MR signals and the MRI parameters derived from the measured MR parameters. For example, a DUTE $R2^*$ computation potentially varies depending on the TEs employed to obtain the MR imaging data, such as the water-fat in-phase or out-of-phase TEs used to obtain the second echo of a the DUTE sequence, and consequently potentially yields different $R2^*$ signals for different MRI scanners.

Images obtained using these additional direct MR imaging methods are also vulnerable to misclassification between bone/air and air/CSF interfaces due to poor imaging contrasts among these different tissue types. For example, the segmentation of tissues based on $R2^*$ images often results in major misclassifications in the sinus regions due to susceptibility effects near air-tissue interfaces. Further, bone and adipose tissue cannot be effectively separated using $R2^*$ signals or inverse logarithm of ZTE signals.

Further, these additional direct MR imaging methods assign constant values of parameters representative of tissue properties, such as linear attenuation coefficients (LACs) used in PET imaging data analysis, and thus fail to capture the heterogeneity of bone, soft and adipose tissue attenuation properties. For example, within the brain, the differences between LAC values of gray matter (GM), white matter (WM), and cerebrospinal fluid (CSF) have been assumed to be low and therefore not likely to affect attenuation correction accuracy. However, since photon attenuation is a function of both LAC values and the thickness of tissue, the sheer amount of tissue present could introduce errors into the PET reconstruction if a homogeneous LAC distribution is assumed.

SUMMARY

In one aspect, a DUFA-MUTE MRI system configured to obtain a pseudo-CT image of at least a portion of a patient is provided that includes an MRI scanner and a computing device operatively coupled to the MRI scanner, the computing device that includes at least one processor and a computer-readable media. The computer-readable media encodes a plurality of modules. Each module of the plurality of modules includes a plurality of instructions executable by the at least one processor. The plurality of modules includes an MR signal acquisition module configured to operate an MRI scanner according to a DUFA-MUTE MRI sequence and to receive a plurality of MR signals associated with a plurality of voxels within the at least a portion of the patient. The plurality of modules also includes an MR signal processing module configured to calculate at least one MRI parameter for each voxel of the plurality of voxels based on a portion of the plurality of MR signals associated with that voxel. The at least one MRI parameter includes R1. The plurality of modules further includes a segmentation module configured to assign a tissue type to each voxel based on at least a portion of the at least one MRI parameter associated with that voxel according to a plurality of tissue assignment criteria. The plurality of modules additionally includes a Hounsfield unit conversion module configured to assign an HU value to each voxel based on the assigned tissue type and the at least one MR parameter associated with that voxel. The plurality of modules further additionally includes a pseudo-CT image reconstruction module configured to produce the pseudo-CT image that includes a map of the plurality of voxels and associated HU values.

In another aspect, a method for obtaining a pseudo-CT image of at least a portion of a patient is provided. The method includes obtaining a plurality of MR signals from a plurality of voxels within the at least a portion of the patient according to a DUFA-MUTE MRI sequence. The DUFA-MUTE MRI sequence includes a first multiple ultrashort echo time sequence characterized by a first flip angle FA1, a first echo time TE1 and a second echo time TE2, and further includes a second multiple ultrashort echo time sequence characterized by a second flip angle FA2, the first echo time TE1 and the second echo time TE2. The method also includes calculating at least one MRI parameter for each voxel of the plurality of voxels based on a portion of the plurality of MR signals associated with that voxel. The at least one MRI parameters includes R1. The method further includes assigning a tissue type to each voxel based on at least a portion of the at least one MRI parameter associated with that voxel according to a plurality of tissue assignment criteria. The method additionally includes assigning an HU value to each voxel based on the assigned tissue type and the at least one MR parameter associated with that voxel, and producing the pseudo-CT image comprising a map of the plurality of voxels and associated HU values.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings illustrate various aspects of the disclosure.

DETAILED DESCRIPTION

Figure 1:
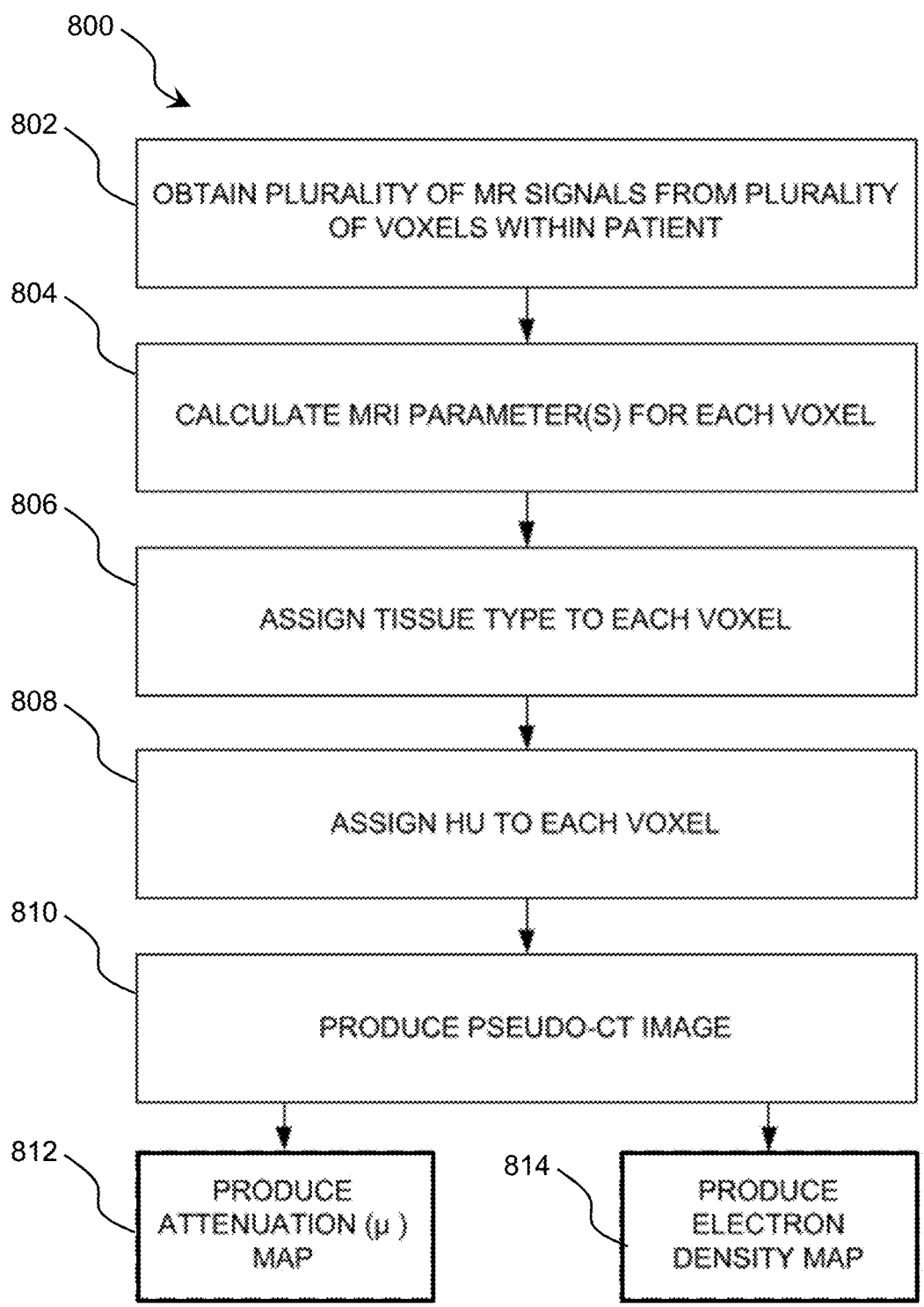
FIG. 1 is a flowchart illustrating the steps of a method for obtaining a pseudo-CT image of bone tissue using DUFA-MUTE MR imaging data in one aspect.

In various aspects, systems and methods for obtaining pseudo-CT images of at least a portion of a patient are disclosed. Pseudo-CT images, as used herein, refer to images comprising 2D or 3D maps of an estimated Hounsfield unit over a plurality of voxels positioned within a selected area or volume from the patient. As described in additional detail below, each estimated Hounsfield unit of each voxel within the pseudo-CT image is assigned based on at least one MRI parameter calculated from a plurality of MR signals obtained from the patient using an MRI scanner. In various additional aspects, the disclosed systems and methods further produce additional 2D or 3D maps including, but not limited to, attenuation maps and electron density maps based on the pseudo-CT images.

The disclosed systems and methods make use of MR images obtained using a dual flip angle, multi-echo ultra-short echo time (DUFA-MUTE) MRI sequence. The DUFA-MUTE MRI sequence, described in detail below, is an extension of previous fat suppression methods, such as the Dixon technique, that enables rapid and robust patient-specific MR imaging. The DUFA-MUTE MRI further enables accurate segmentation of various tissue types, including, but not limited to, bone tissue, within a variety of imaging regions of the patient including, but not limited to, brain, head/neck, and pelvis, in which segmentation at bone/air and bone/soft tissue interfaces are challenging.

The systems and methods disclosed herein overcome many of the limitations of previous methods associated with a variety of MRI systems and MR-assisted imaging or treatment systems such as combined PET/MRI systems, in particular those limitations associated with the MR imaging of bone. The disclosed systems and methods enable the accurate segmentation of a variety of different tissue types including, but not limited to, air, bone, fat, and soft tissues including, but not limited to, grey matter, white matter, cerebrospinal fluid (CSF), ligaments, tendons, muscles, and various organs such as livers, lungs, and kidneys. In some aspects, the pseudo-CT images produced using the disclosed systems and methods form the basis for additional patient-specific parameter maps including, but not limited to, linear attenuation coefficient (LAC) maps useful in PET imaging and electron density maps useful for the planning and administration of various treatments including, but not limited to, radiotherapy.

I. Method of Obtaining Pseudo-CT Images Using DUFA-MUTE MRI

In various aspects, MR imaging is performed using the DUFA-MUTE MRI sequence and the measured MR signals are analyzed to produce CT-like images of bone tissue, as well as various other soft tissues (i.e. pseudo-CT images), within various regions of a patient including but not limited to: pelvis, spine, and/or cranium.

In one aspect, the DUFA-MUTE MR imaging method described herein enables the acquisition of pseudo-CT images without exposing the patient to x-ray radiation. Further, the DUFA-MUTE MR imaging method includes partitioning MR imaging data into various tissue types including bone tissue as well as other soft tissues including, but not limited to, brain tissues, muscle tissue, ligaments, liver tissues, lung tissues, and other organ tissues, thereby enabling the visualization of interacting bones and soft tissues in a single image without need for additional registration of different images such as MR images and CT images.

In another aspect, the DUFA-MUTE MR imaging method provides an additional basis by which images produced by different imaging modalities are spatially registered to one another. Although significant effort has been put into the development of MR-based tissue segmentation, in particular to develop MR-based attenuation coefficients (MRAC) for combined PET/MR imaging in the cranium, the development of MR-based tissue segmentation of bone tissue for body imaging is less fully realized. As compared to the cranium and brain, there exists a higher degree of variation in the anatomy and body poses across patients in body imaging of structures such as the pelvis and appendages. This increased variation poses a fundamental challenge to image registration in body imaging, and as a result, MR-based bone tissue segmentation, and consequently combined PET/MR imaging using MRAC has not been developed at a comparable level for body imaging. The challenge of registration of body structures that include bone tissue in regions outside of the cranium additionally limit the application of atlas-based MRAC approaches described above for combined PET/MR imaging of the body. The DUFA-MUTE MR imaging method for imaging bone tissue disclosed herein obviates many of the limitations of existing methods of MR-based bone imaging of the body.

Challenges for obtaining suitable MR-based pseudo-CT images in the head region of a patient include proper identification of the location of bone tissue within the region to be imaged. Proper delineation of bone is of particular importance in neurological PET imaging due to the relatively high prevalence of bone found in the head and spine regions within which reside many neurological structures of interest. Bone tissue is a particularly effective attenuator (per unit volume) of the photons associated with PET imaging, and relatively minor errors in estimating the amount of bone tissue within a region to be imaged using PET imaging methods potentially lead to relatively large underestimations of PET signal, particularly in those tissues adjacent to bone. However, due to its low spin proton density and short $T2/T2^*$ relaxation time, bone tissue usually exhibits near-zero signals in conventional MR images, rendering bone tissue particularly challenging to locate using MR methods.

FIG. 1 is a flow chart illustrating a method 800 of obtaining pseudo-CT images using DUFA-MUTE MR imaging. In one aspect, the method 800 includes obtaining MR signals for a plurality of voxels within at least a portion of the patient using a DUFA-MUTE MRI sequence at 802. The MR signals obtained at 802 for each voxel are further processed to calculate at least one MRI parameters that is assigned to each voxel at step 804. Each of the at least one MRI parameters calculated at 804 are used to assign a tissue type to each voxel at 806. Based on each voxel's MRI parameters assigned calculated at 804 and/or tissue type assigned at 806, a Hounsfield unit (HU) value is calculated and assigned to each voxel at 808. The plurality of voxels and associated HU values are assembled to reconstruct the pseudo-CT image at 810. In another aspect, the HU values of the pseudo-CT image produced at 810 are used to produce an attenuation map at 812. In another additional aspect, the HU values of the pseudo-CT image produced at 810 are used to produce an electron density map at 814.

A) Obtain MR Signals Using DUTE-MUTE MRI Sequence

Referring again to FIG. 1, the method 800 includes performing MR imaging by obtaining a plurality of MR signals at 802 using a DUFA-MUTE MRI sequence to image bone tissue directly along with other tissues including, but not limited to: water, fat, grey matter, white matter, CSF, and air in various aspects. In one aspect, the DUFA-MUTE MRI sequence includes acquiring MR signals using a dual ultra-short echo time (UTE) MRI sequence at two different flip angles (FAs). In this aspect, MR signals at two echo times (TE1 and TE2) are collected at a first flip angle (FA1), and then additional MR signals are collected at TE1 and TE2 for a second flip angle FA2.

In various aspects, the flip angles FA1 and FA2 characterizing the DUFA-MUTE MRI sequence are selected to enhance the sensitivity and/or contrast of the MR signals for bone tissues as well as any additional tissue types within the region to be imaged including, but not limited to: bone, fat, air, white matter, grey matter, cerebrospinal fluid (CSF), muscle, tendon, and various organs, such as kidneys and lungs. In one aspect, the flip angles FA1 and FA2 are selected to provide MR signals with sufficient signal strength and contrast to enable detection and differentiation of the bone and additional tissue types described herein from one another. The selected flip angles FA1 and FA2 characterizing various aspects of the DUFA-MUTE MRI sequence facilitate accurate partitioning of tissue types within the imaged region.

Figure 2:
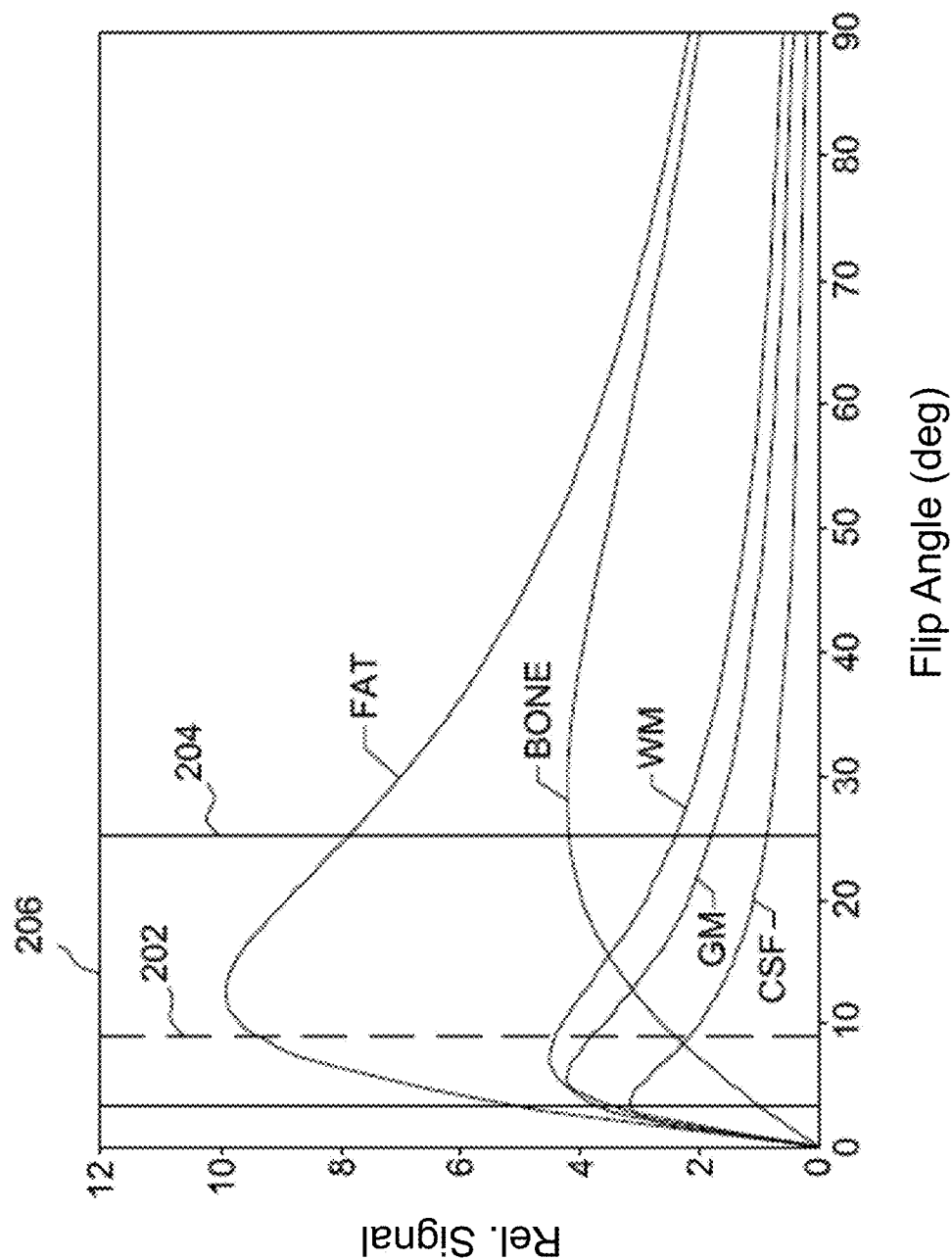
FIG. 2 UTE (ultra-short echo time) MR signal intensities in bone, cerebrospinal fluid (CSF), grey matter (GM), white matter (WM), and adipose tissue as a function of flip angle at a repetition time (TR) of 9 ms.

Without being limited to any particular theory, different tissue types are typically characterized by MR signal strengths that are influenced at least in part by the flip angle of the MRI sequence used to obtain the MR signals. FIG. 2 is a graph summarizing the relative strengths of MR signals obtained for different tissue types as a function of flip angle (FA) at a repetition time (TR) of 9 ms, representative of MR signals associated with T1-contrast MR imaging. At FA=9° (denoted as vertical line 202) the strengths of the MR signals produced by bone tissue, cerebrospinal fluid (CSF), and soft tissues such as grey matter (GM) and white matter (WM) do not possess sufficient contrast to enable unambiguous partitioning of these tissue without additional information. A UTE MRI sequence conducted at FA=25° (denoted as vertical line 204) yields large MR signal magnitudes for bone tissue, but CSF signal magnitudes are low, which results in a possible misclassification between CSF and air (noise). On the other hand, CSF signal is more than three times higher at an FA of 3° when compared to an FA of 25°.

In order to segment all tissues, the dual FA multi-echo (DUFA-MUTE) MR imaging acquires MR signals at two flip angles in various aspects. In one aspect, the two flip angles are selected to provide MR signals that are compared as described herein below to unambiguously assign a tissue type to each voxel as part of the partitioning process. In one aspect, the first FA (FA1) is selected to enhance the contrast between CSF and air MR signals, and the second FA (FA2) is selected to provide a strong bone MR signal relative to MR signals from other tissue types. In an additional aspect, the DUFA-MUTE MRI sequence is conducted at flip angles FA1=3° and FA2=25°.

In various other aspects, the DUFA-MUTE MRI sequence is characterized by multiple echo times TE1, TE2, and TE3. In one aspect, the first echo time (TE1) is selected to fall within an ultrashort echo time (UTEs) selected to capture MR signals at relatively high magnitude from bone, and additional echo times (TE2 and TE3) are selected to fall after the relaxation time of bone. In an aspect, the DUFA-MUTE MRI sequence acquires one image at an ultra-short echo time (TE=0.07 ms) and additional images at longer echo times. Because of the short relaxation time of the bone, MR signals characteristic of bone tissue are detectable at the first echo, but are greatly diminished at the subsequent echoes. The presence and absence of bone signal in the DUTE images reconstructed from the MR signals detected at the first echo and subsequent echoes, respectively, allow for a segmentation of bone in addition to the soft tissue segmentation attained using MR imaging methods.

In various other aspects, TE1, TE2, and TE3 are further selected to facilitate the partitioning of fat from water-containing tissues. In one aspect, TE1, TE2, and TE3 are selected to facilitate partitioning of fat and water-containing tissues using alternative water-fat in-phase and out-of-phase TEs, an approach analogous to existing two-point or three-point Dixon sequences. In this aspect, TE1, which is typically an ultrashort echo time, is selected to acquire MR signals of fat and of water-containing tissues that are in phase with one another. In addition, TE2 and TE3 are selected to acquire MR signals of fat and of water-containing tissues that are in-phase or 180° out-of-phase with one another. As described herein below, images produced using the MR signals from TE1, TE2, and TE3 are added or subtracted to partition fat and water-containing tissues according to known signal processing methods associated with the three-point Dixon approach. In various aspects, the multi-echo images will be acquired at alternatively water-fat in-phase and water-fat out-of-phase echo times. In one aspect, the DUFA-MUTE MRI sequence includes TE1=0.07 ms, TE2=2.46 ms, and TE3=3.69 ms. In various aspects, the selection of FA1 and FA2 will be adjusted to optimize the separation of bone, soft tissue, air and CSF depending on the T1 of each of these compartments.

In various other aspects, the DUFA-MUTE MRI sequence includes three or more flip angles and three or more echo times. The additional echo times and/or flip angles are selected to enhance contrast and/or MR signal strength of a particular tissue type. In an aspect, the number of additional flip angles and/or echo times in excess of two are influenced by any one or more of a plurality of factors including, but not limited to: various imaging parameters, scan time, overall data acquisition time, data processing time, processor and memory capacity of the computing device or devices used to acquire and process the MR data, and any other relevant factor. Non-limiting examples of imaging parameters that influence the selection of flip angles and/or echo times include: repetition time TR, overall scan time, required spatial resolution, and the scanned body parts.

B) Calculate MRI Parameters from MR Signals

Figure 3:
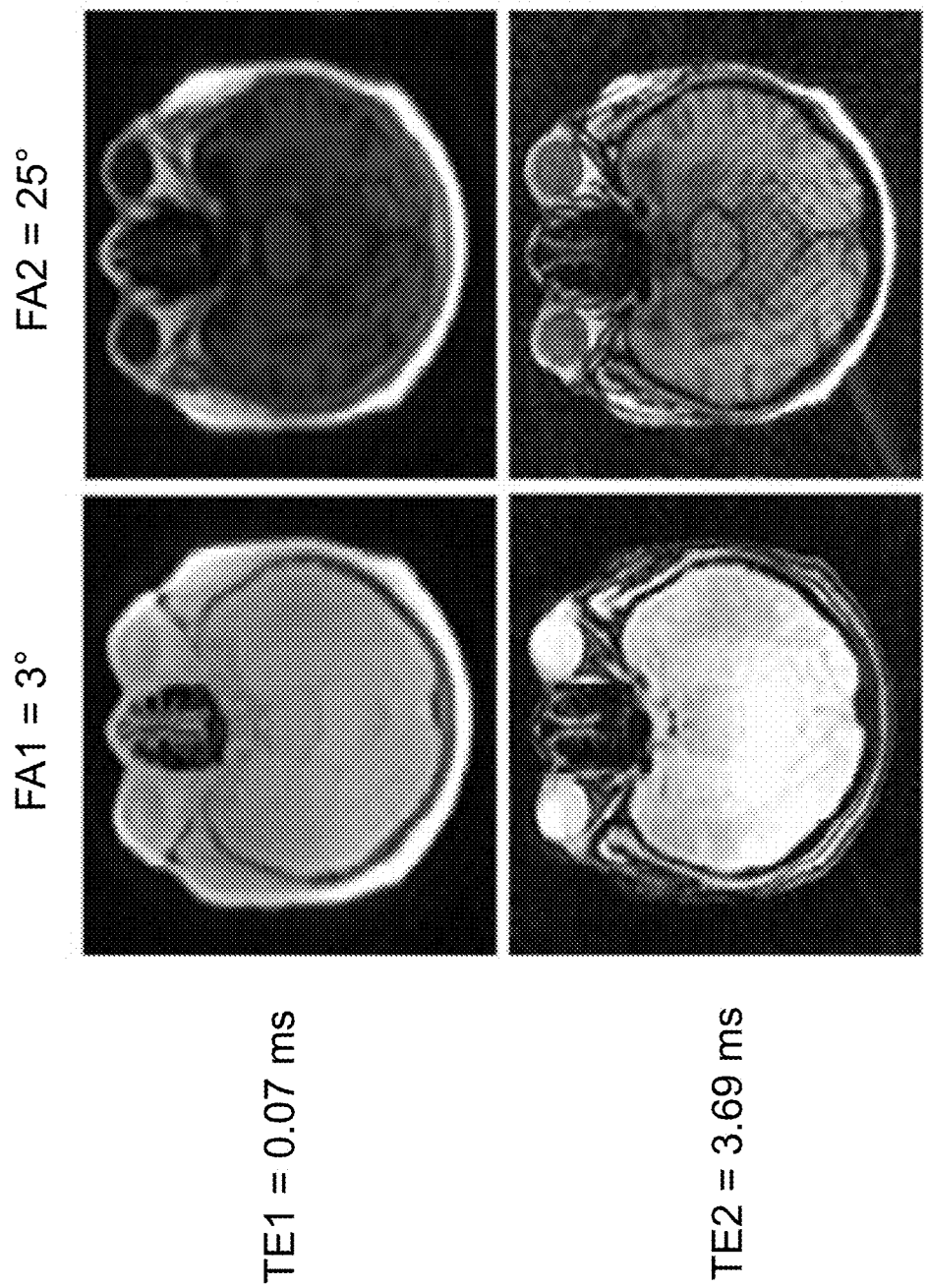
FIG. 3 is a series of representative DUFA-MUTE images obtained at flip angles of 3° and 25°, as well as at echo times of 0.07 ms and 3.69 ms.

Referring again to FIG. 1, the method 800 further includes processing the MR signals measured at each voxel at 802 to calculate at least one MRI parameter at 804. FIG. 3 shows representative images produced from MR signals using the DUFA-MUTE MRI sequence described above in one aspect that includes: FA1=3°, FA2=25°, TE1=0.07 ms, and TE2=3.69 ms. The 2×2 array of images shown in FIG. 3 encodes a significant amount of information and is further analyzed to compute one or more MRI parameters. The one or more MRI parameters calculated for each voxel are associated with that voxel. The plurality of voxels and the one or more MRI parameters associated with each voxel are assembled to produce the one or more MRI parameter maps similar to the images shown in FIG. 3.

In various aspects, any MRI parameter suitable for partitioning a region of interest into different tissue types and/or diagnosing a disorder is optionally calculated at 804. Non-limiting examples of suitable MRI parameters calculated at 804: R1, R2*, $iUTE_{FA1}$, $iUTE_{FA2}$, $WATER_{FA1}$, $FAT_{FA1}$. In various aspects, R1 is calculated as the inverse of T1 (R1=1/T1), wherein T1 is a spin-lattice relaxation time obtained from the dual flip angle UTE scans using methods known in the art. R2* is the inverse of the rate of spin-spin relaxation calculated based on Equation 1, shown below, using MR signals detected from multiple echoes for both water and fat components using methods known in the art. $iUTE_{FA1}$ and $iUTE_{FA2}$ are the inverses of first echo at the first and second flip angle FA1 and FA2, respectively. $WATER_{FA1}$ and $FAT_{FA1}$ are the water and fat signals obtained at the first flip angle flip one using MR signals detected from at least two echoes including, but not limited to, a first echo in which the MR signals from water and fat are in phase with one another, and MR signals detected from a second echo in which the MR signals from water and fat are 180° out of phase with one another according to methods related to existing fat suppression methods such as 2-point or 3-point DIXON MRI sequence imaging.

Figure 4:
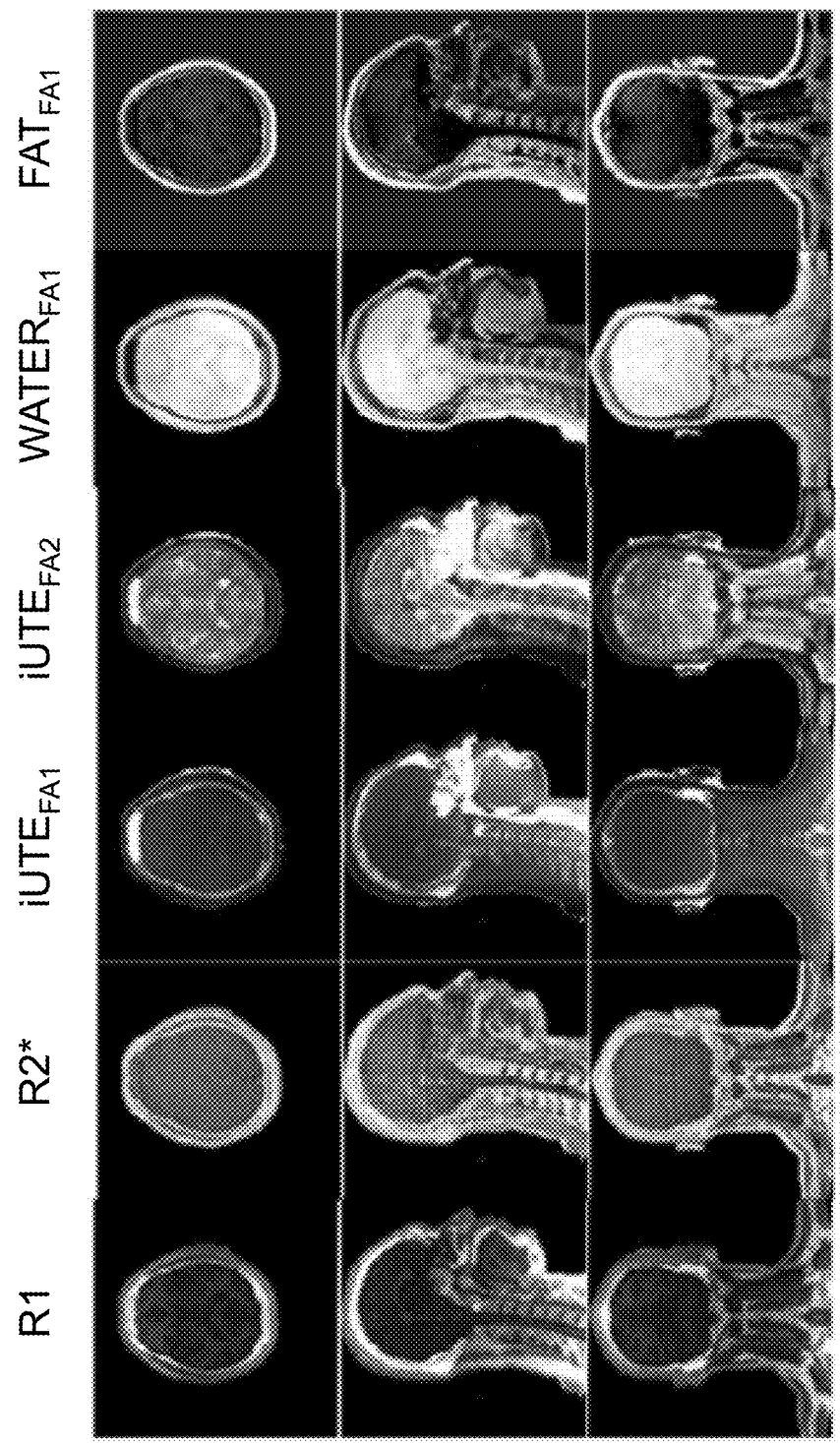
FIG. 4 is a series of parametric maps computed using the DUFA-MUTE images, including transverse (top row), sagittal (middle row) and coronal (bottom row) views with contrast based on R1, R2*, inverse of the ultrashort echo times at flip angles of 3° (iUTE$_{FA1}$) and 25° (iUTE$_{FA2}$), water signal at a flip angle of 3° (WATER$_{FA1}$) and fat signal at a flip angle of 3° (FAT$_{FA1}$).

FIG. 4 includes a series of images showing maps of individual MRI parameters calculated as described above in one aspect based on MR signals obtained using the DUFA- MUTE MRI sequence described above with a first flip angle (FA1) of 3° and a second flip angle (FA2) of 25°. Each column of images shown in FIG. 4 corresponds to one of the individual MRI parameters (R1, R2*, iUTE$_{FA1}$, iUTE$_{FA2}$, WATER$_{FA1}$, and FAT$_{FA1}$) shown in three views: a transverse plane (top row of images), a mid-sagittal plane (middle row) and a coronal plane (bottom row).

Figure 5:
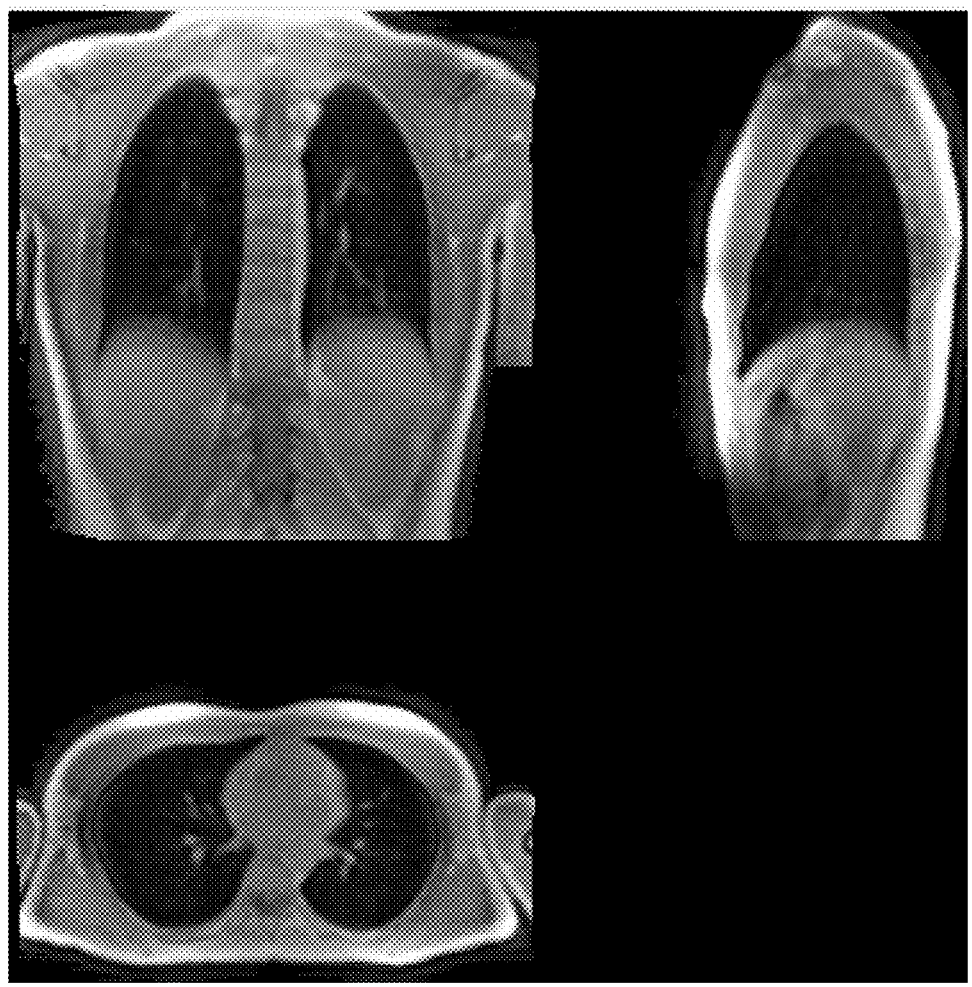
FIG. 5 contains images of MR signal maps of a thorax reconstructed from a three-minute DUFA-MUTE acquisition for TE=0.07 ms, FA=3 degrees, and TR=5 ms.
Figure 6:
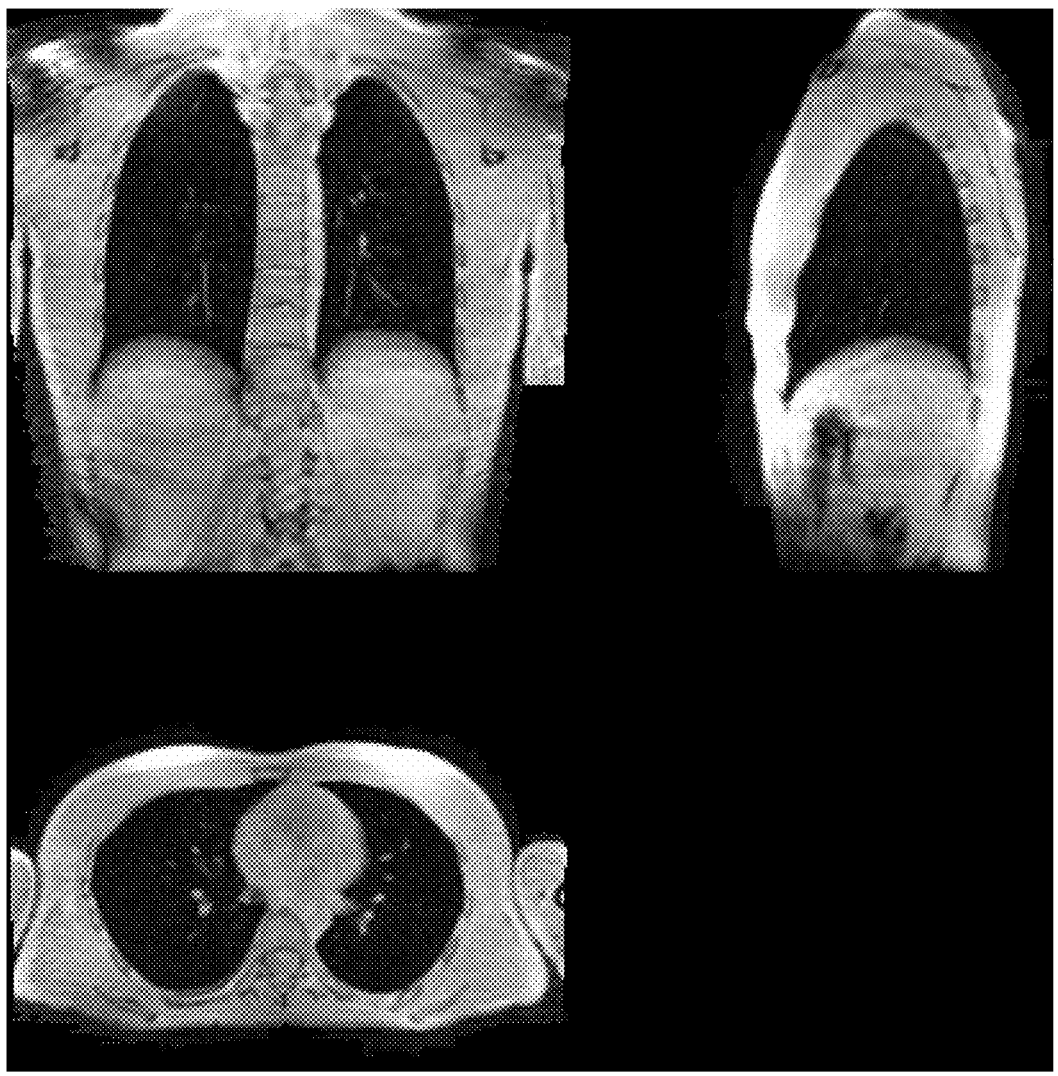
FIG. 6 contains images of MR signal maps of a thorax reconstructed from a three-minute DUFA-MUTE acquisition for TE=2.46 ms, FA=3 degrees, and TR=5 ms.
Figure 7:
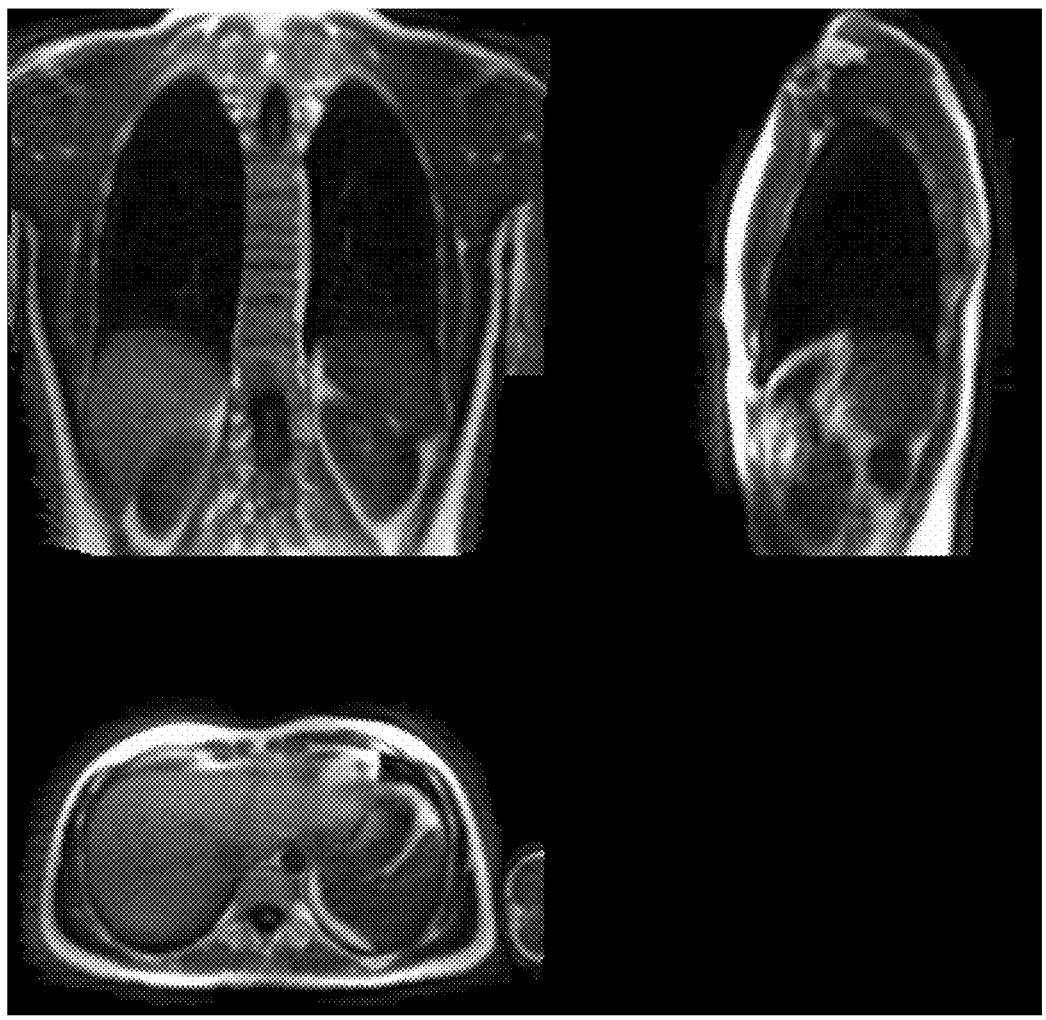
FIG. 7 contains images of MR signal maps of a thorax reconstructed from a three-minute DUFA-MUTE acquisition for TE=0.07 ms, FA=15 degrees, and TR=5 ms.
Figure 8:
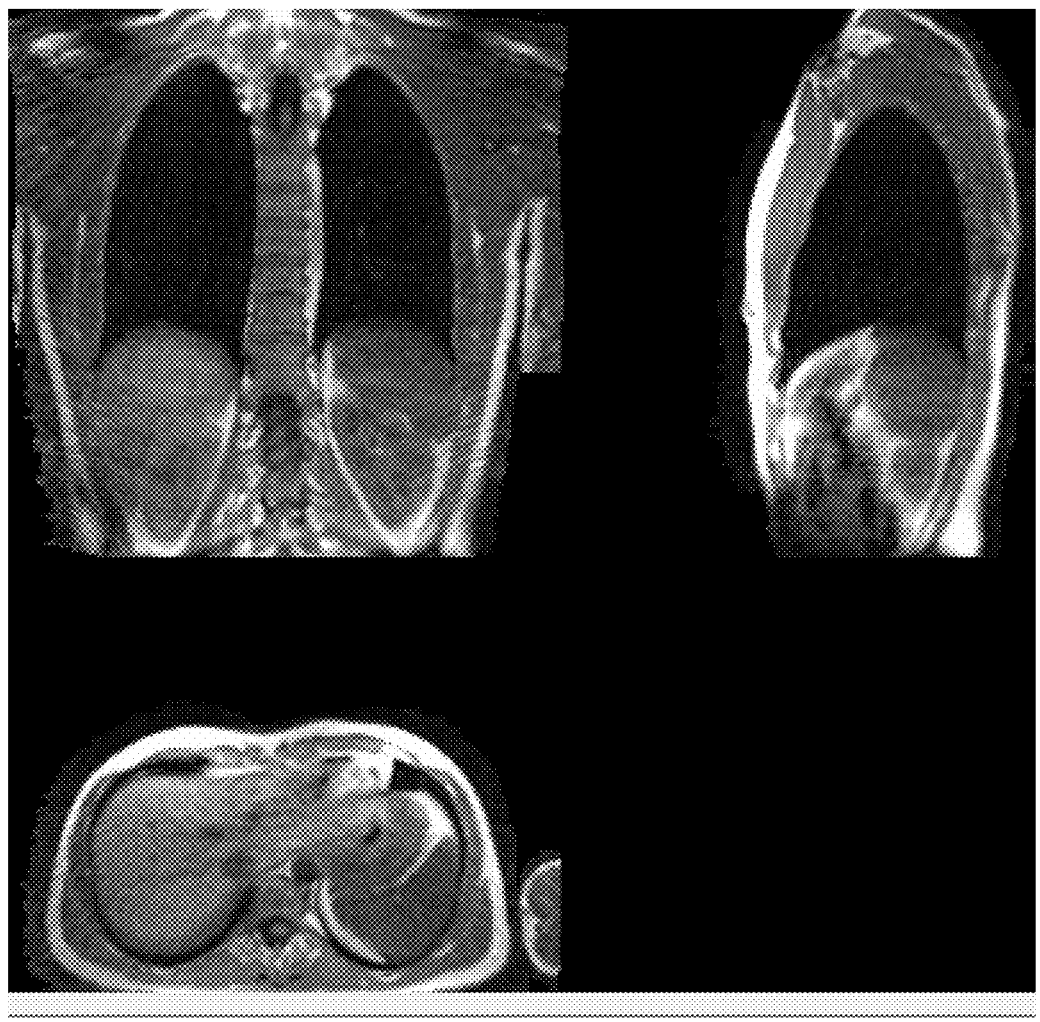
FIG. 8 contains images of MR signal maps of a thorax reconstructed from a three-minute DUFA-MUTE acquisition for TE=2.46 ms, FA=15 degrees, and TR=5 ms.
Figure 9:
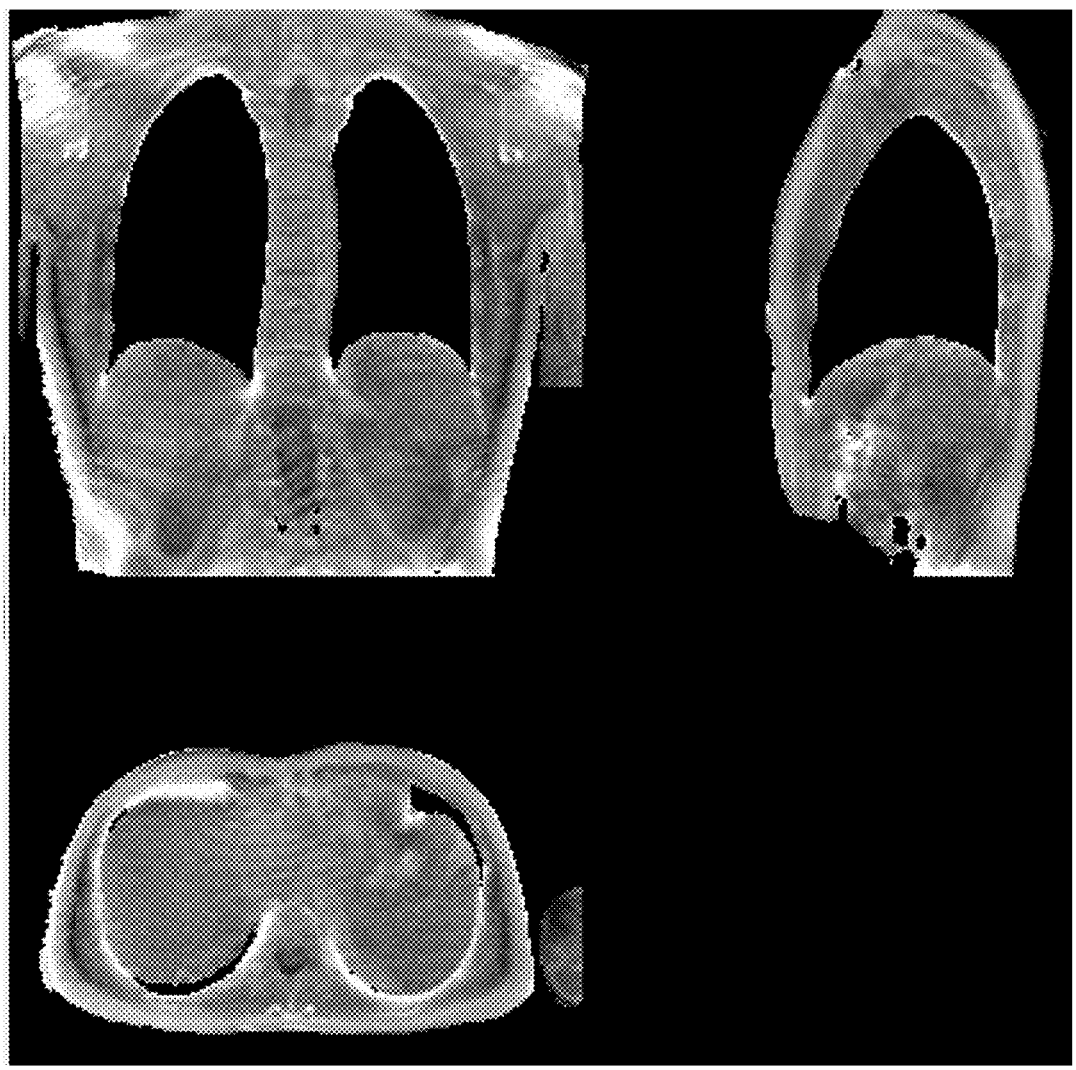
FIG. 9 contains images of R2* maps of a thorax derived using the MR signal maps shown in FIG. 7 and FIG. 8.
Figure 10:
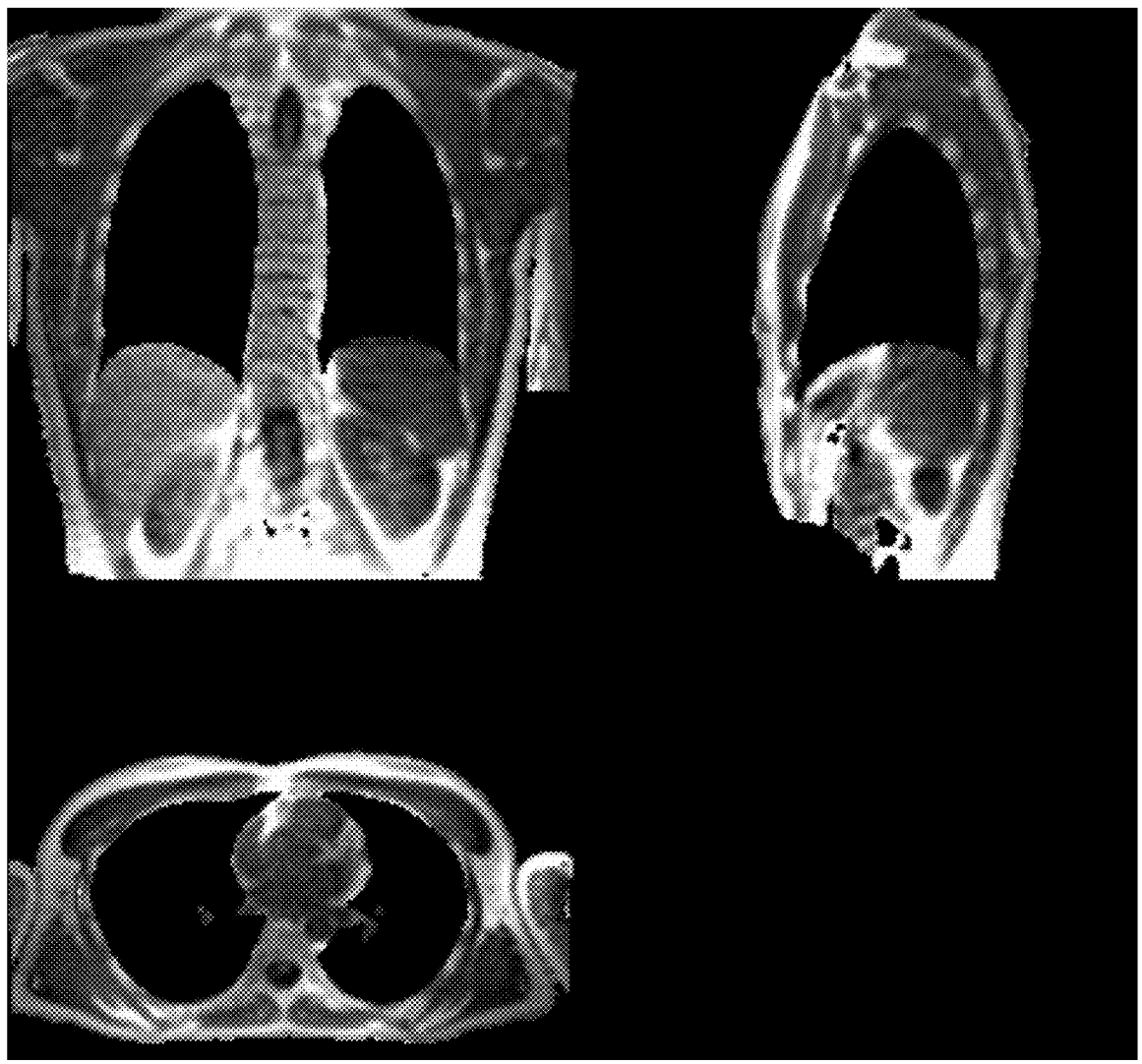
FIG. 10 contains images of R1 maps of a thorax derived using the maps shown in FIG. 5 and FIG. 7.

FIGS. 5, 6, 7, 8, 9, and 10 each include a series of three image views showing one MRI parameter calculated as described above. The MR signals used to calculate the MRI parameters were obtained using a 3-minute MR data acquisition from a thorax region of a patient using a DUFA-MUTE MRI sequence characterized by: TE1=0.07 ms, TE2=2.46 ms, TR=5 ms, FA1=3 degrees, and FA2=15 degrees. Each of the above figures includes one MRI parameters shown mapped in three views: a transverse plane (bottom left image), a mid-sagittal plane (top right image) and a coronal plane (top left image). FIG. 5 shows maps of the MR signal obtained at TE1/FA1. FIG. 6 shows maps of the MR signal obtained at TE2/FA1. FIG. 7 shows maps of the MR signal obtained at TE1/FA2. FIG. 8 shows maps of the MR signal obtained at TE2/FA2. FIG. 9 shows maps of R2*, and FIG. 10 shows maps of R1.

Without being limited to any particular theory, known ultrafast echo time (UTE) MRI sequences assume that regions of bone tissue exhibit faster transverse decay characteristics compared to soft tissues. As a result, the MR signals originating from bone tissue are isolated by comparing two or more MR signals obtained at TE1, TE2, and TE3 of a DUFA-MUTE MR sequence. The MR image obtained at TE1 is presumed to include MR signals from bone tissue as well as other soft tissues, and the MR image obtained at TE2 or TE3 is presumed to include MR signals from only the other soft tissues because TE2 or TE3 is selected to be beyond the relaxation time for bone tissue. In one aspect, R2* is computed according to Equation (1):

$$R2^* = \frac{\ln(K \cdot ECHO1) - \ln(ECHO2)}{TE2 - TE1} \qquad \text{Equation (1)}$$

where: ECHO1 and ECHO2 are the MR signal values for the first and second echoes (both obtained at the same flip angle with water-fat in-phase); TE1 and TE2 are the echo times corresponding to ECHO1 and ECHO2; and K is a correction factor to ensure that no negative values of R2* are computed by Equation (1). In one aspect, the MR signal values ECHO1 and ECHO2 are obtained at a flip angle of about 25° to enhance the contrast of bone tissue with other soft tissues as described herein above. In one aspect, TE2, TE3, or any subsequent echo times of a DUFA-MUTE MRI sequence is used as TE2 in Equation (1) above, and the corresponding MR signals obtained at TE2, TE3, or any subsequent echo times are used as ECHO2 in Equation (1) above to computed R2*.

Without being limited to any particular theory, low voxel intensities in the MR images obtained at TE1 of the DUFA-MUTE MRI sequence (typically an ultra-lower echo time), presumably due to eddy current effects, result in negative R2* values as computed by Equation (1) in some imaging regions of interest without correction (i.e. K=1). To perform a correction for this phenomenon in post-processing, the ECHO1 image is scaled by an empirically-determined factor (K) during R2* computation according to Equation 1. In various aspects, K is selected as the smallest factor that ensured most voxels displayed a higher signal intensity in the ECHO1 image relative to the ECHO2 image, resulting in positive R2* values for all voxels of the parametric map.

The inverse of first echo at the first flip angle (iUTE$_{FA1}$), especially at a first flip angle FA1 of 3°, is characterized by highest signal values in air spaces, relatively high signal values in bone (lower than air spaces but higher than soft tissue and CSF), and relatively low signal values in soft tissue and CSF. On the other hand, the inverse of first echo at the second flip angle (iUTE$_{FA2}$), especially at a second flip angle FA2 of 25° (iUTE$_{FA2}$) is characterized by very high signal values in air, relatively high signal values in CSF (lower than air spaces but higher than soft tissue and bone), but relatively moderate signal values in bone and soft tissue. Combining these two images, a distinct separation between all four tissue classes is observed. Both water and fat signals are computed from the in-phase and out-of-phase images using a method similar to the method associated with the known Dixon MRI sequence, in which the in-phase and out-of-phase images are added to obtain one of the water/fat components and are subtracted to obtain the other water/fat component. In various aspects, the combined information of R1, R2*, iUTE, water signal and fat signal can provide robust and accurate segmentation of bone, air, CSF and soft tissue.

C) Assign Tissue Types to Plurality of Voxels in Region of Interest

Referring again to FIG. 1, the method 800 further include assigning a tissue type to each of the plurality of voxels at 806 based on a comparison of the MRI parameters calculated for each voxel at 804. As described previously, the MRI parameters are selected to facilitate the identification of the tissue type within each voxel of the region of interest.

Figure 11:
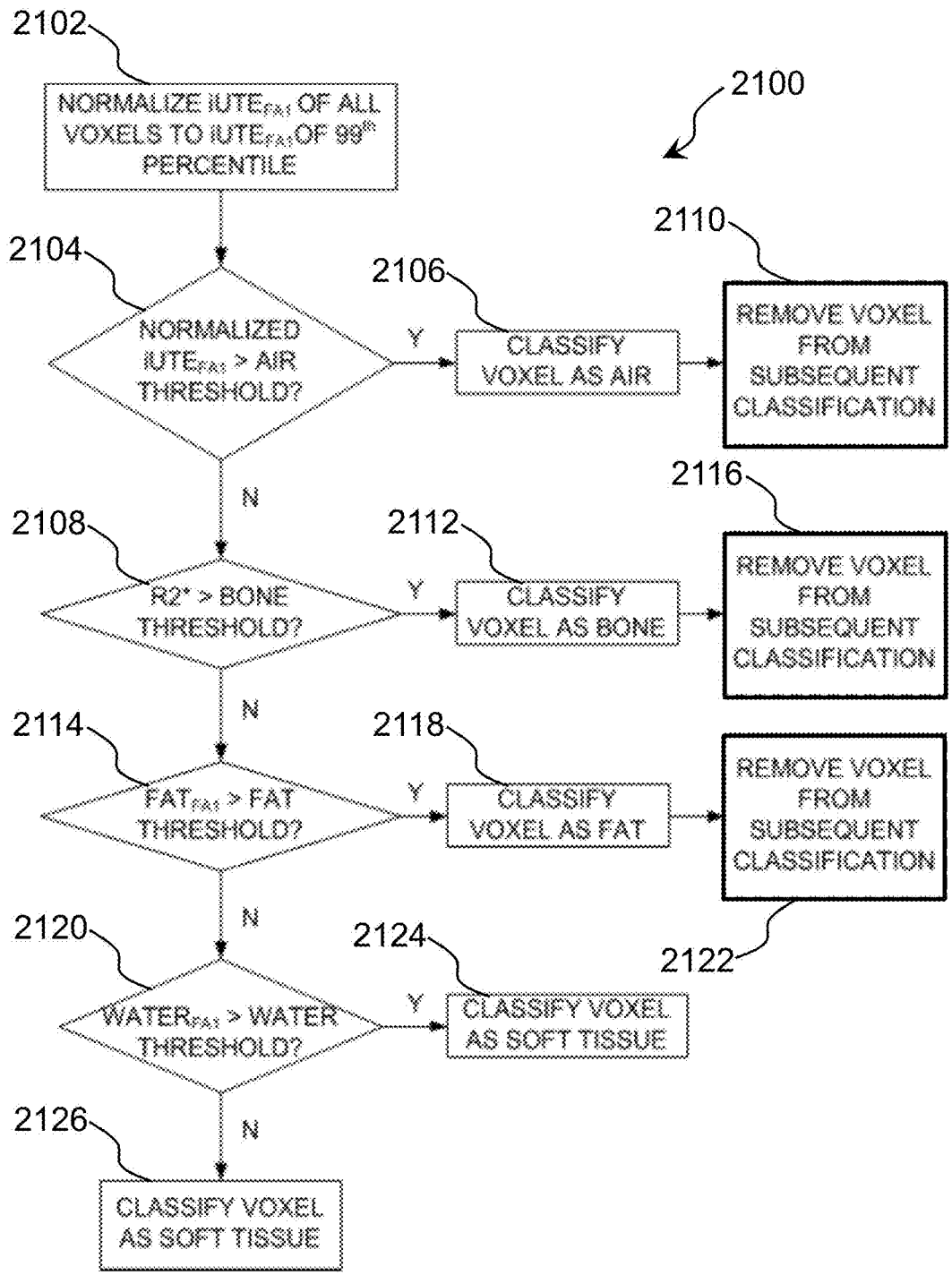
FIG. 11 is a flow chart illustrating a method of segmenting tissues based on various MRI parameters according to one aspect of the disclosed method.

FIG. 11 is a flow chart illustrating a method 2100 of segmenting tissues in one aspect. In various aspects, a voxel is identified as containing air by analysis of an MR signal comprising the inverse of first echo at the first flip angle (iUTE$_{FA1}$). Without being limited to any particular theory, it is thought that the iUTE$_{FA1}$ is largely due to air in the presence of bone, fat, and soft tissues typical of the regions of interest of a patient. In one aspect, iUTE$_{FA1}$ is obtained at a first flip angle (FA1) of 3°. In one aspect, the voxel-wise multiplicative inverse of the image reconstructed from the first (UTE) echo obtained at the first flip angle (FA1) to obtain the iUTE$_{FA1}$ image.

Referring again to FIG. 11, all voxels within the iUTE$_{FA1}$ image are normalized to a 99th percentile value at 2102, and those voxels with normalized iUTE$_{FA1}$ values above an air threshold value at 2104 are classified as containing air at 2106. In one aspect, the air threshold value is about 0.06. In another aspect, the air threshold value in the iUTE$_{FA1}$ images are determined using histogram analysis performed using methods known in the art to preferentially select air voxels over bone and CSF voxels within the iUTE$_{FA1}$ image. Optionally, those voxels classified as air are removed from subsequent analysis at 2110.

In another aspect, the MRI parameter R2* is used to assign the bone tissue type to selected voxels within the parametric map. In one aspect, all voxels within an R2* contrast image having R2* values falling above a bone threshold value at 2108 are assigned a bone tissue type at 2112. In an aspect, the bone threshold value is about 550 s$^{-1}$. In various aspects, the bone threshold value is selected to identify as many voxels containing bone tissue as possible while minimizing the number of fat and CSF voxels included. In another aspect, those voxels assigned a tissue type of air are removed from the R2* analysis at 2110 prior to thresholding the R2* contrast image to identify those voxels associated with bone tissue.

In another aspect, an MRI parameter comprising a fat signal ($FAT_{FA1}$) derived from the in-phase and out-of-phase signals obtained at a first echo time TE1 and a second echo time TE2, respectively, and at a first flip angle FA1 is used to assign a tissue type of fat to a portion of voxels. In an aspect, those voxels with $FAT_{FA1}$ values higher than a fat threshold value at 2114 were classified as fat tissue type at 2118. In one aspect, the fat threshold value is about 250. Optionally, those voxels classified as fat are removed from subsequent analysis at 2118.

In another aspect, the MRI parameters comprising a water signal ($WATER_{FA1}$) derived from the in-phase and out-of-phase signals obtained at a first echo time TE1 and a second echo time TE2, respectively, and at a first flip angle FA1 are used to assign tissue types of soft tissue to the plurality of voxels in the parametric map. In an aspect, those voxels in the parametric map with $WATER_{FA1}$ values higher than a water threshold value at 2120 are classified as soft tissue type at 2124. In one aspect, the water threshold value is about 150. In an additional aspect, any voxel not already classified as air, bone, fat, or soft tissue is classified as soft tissue at 2126. In another additional aspect, any voxel classified as both fat and soft tissue are classified as the fat tissue type.

Figure 12:
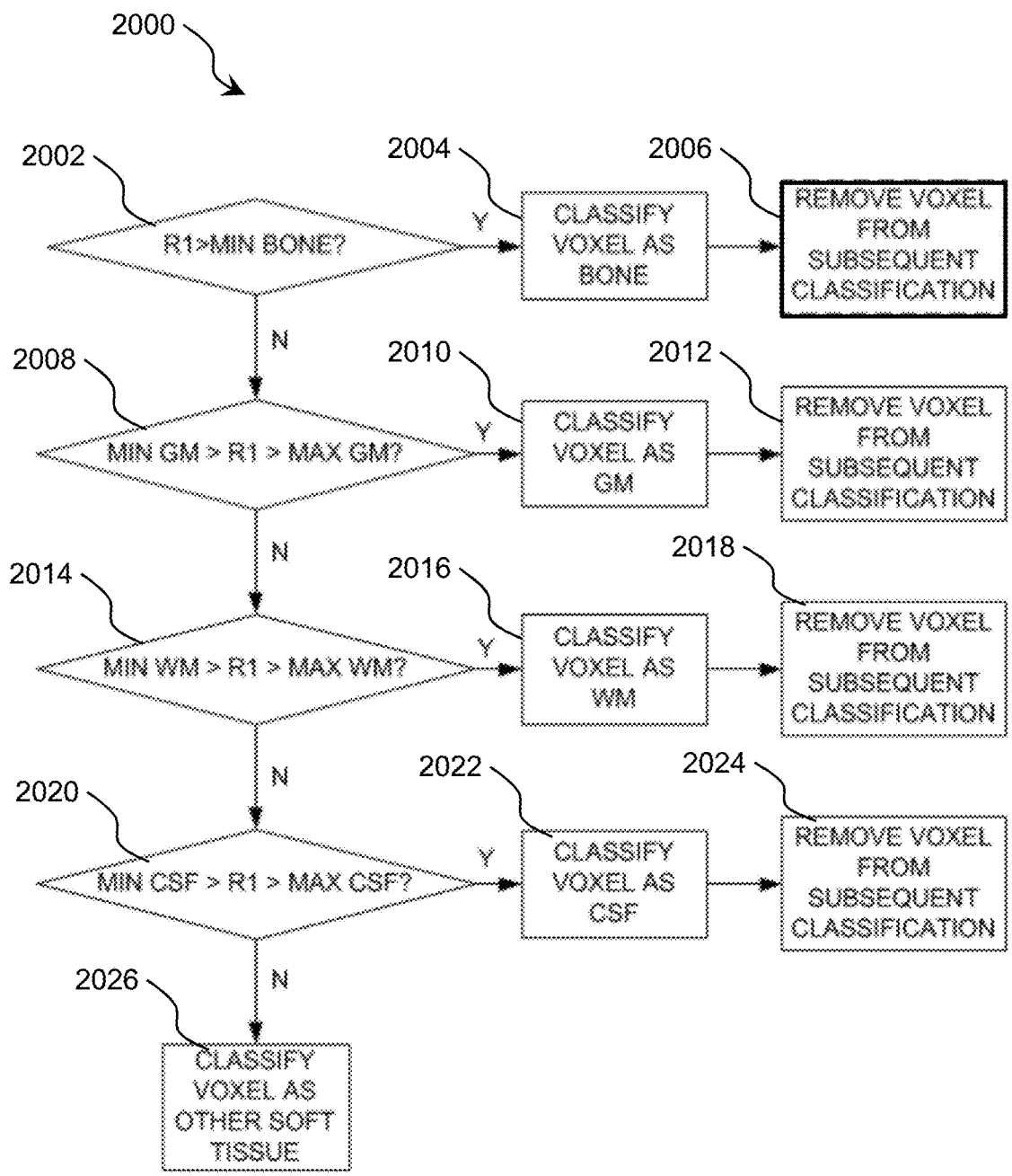
FIG. 12 is a flow chart illustrating a method of segmenting tissues based on R1 according to one aspect of the disclosed method.

In another additional aspect, tissues within a parametric map are segmented using a single MRI parameter comprising R1, defined herein as the inverse of T1. FIG. 12 is a flow chart illustrating a method 2000 of segmenting tissues in this other additional aspect. In this method 2000, R1 (1/T1) maps are computed using the UTE images obtained at the first flip angle FA1 and second flip angle FA2 as described above. In this method 2000, the computed R1 values at each voxel are used for tissue segmentation to separate bone tissue, cerebrospinal fluid (CSF), grey matter (GM) and white matter (WM). In one aspect, a plurality of R1 values corresponding to a plurality of voxels of each known tissue type is used to define a plurality of ranges of R1 values, each range of R1 values corresponding to one tissue type including, but not limited to, bone tissue, CSF, GM, and WM.

Referring again to FIG. 12, voxels having R1 values above a minimum bone value at 2002 are classified as bone tissue at 2004. In one aspect, the minimum bone value is about 5 $ms^{-1}$ Optionally, those voxels classified as bone at 2004 are removed from subsequent classification at 2006. In another aspect (not illustrated), voxels having R1 values ranging from about 5 $ms^{-1}$ to about 25 $ms^{-1}$ are classified as bone tissue.

Referring again to FIG. 12, voxels having R1 values ranging between a minimum GM value and a maximum GM value at 2008 are classified as GM at 2010. In one aspect, the minimum GM value is about 2 $ms^{-1}$ and the maximum GM value is about 4 $ms^{-1}$. Optionally, those voxels classified as GM at 2008 are removed from subsequent classification at 2012.

Referring again to FIG. 12, voxels having R1 values ranging between a minimum WM value and a maximum WM value at 2014 are classified as WM at 2016. In one aspect, the minimum WM value is about 1 $ms^{-1}$ and the maximum WM value is about 2 $ms^{-1}$. Optionally, those voxels classified as WM at 2016 are removed from subsequent classification at 2018.

Referring again to FIG. 12, voxels having R1 values ranging between a minimum CSF value and a maximum CSF value at 2020 are classified as CSF at 2022. In one aspect, the minimum CSF value is about 0.5 $ms^{-1}$ and the maximum CSF value is about 1 $ms^{-1}$. Optionally, those voxels classified as CSF at 2022 are removed from subsequent classification at 2024. In another aspect, those voxels not classified as bone, GM, WM, or CSF are classified as other soft tissue at 2026.

In another aspect, the MRI parameter R1 is used to classify voxels associated with additional tissue types. In this other aspect, MR-derived R1 values obtained from samples of known tissue types are used to determine ranges of R1 values associated with each additional tissue type using methods similar to the methods described above. Non-limiting examples of suitable additional tissue types include liver tissue, lung tissue, muscle tissue, tendon tissue, tumor tissue, and any other suitable tissue type.

Figures 13A, 13B:
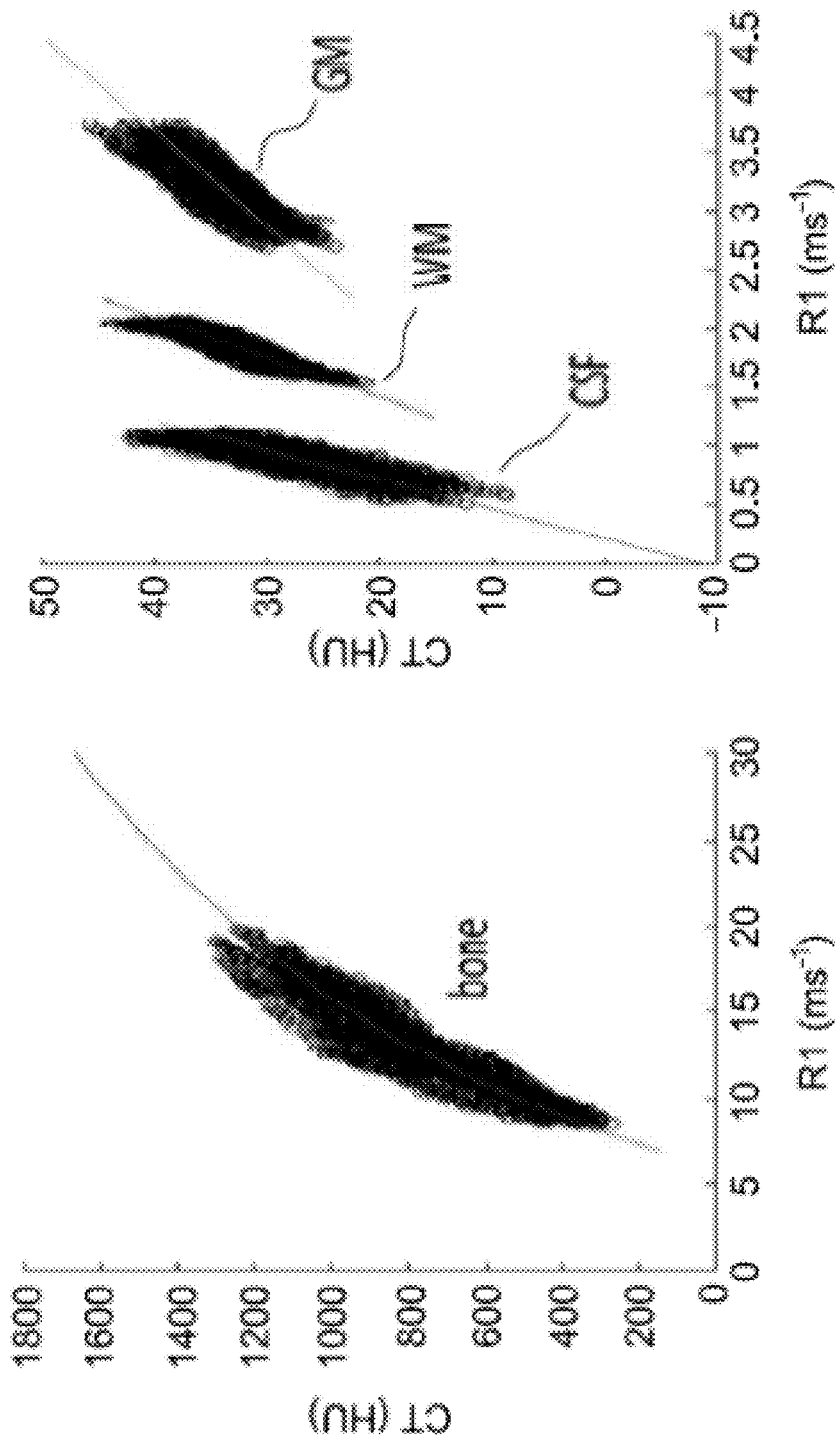
FIG. 13A is a graph of R1 vs. CT-based Hounsfield Units (HU) in bone.
FIG. 13B is a graph of R1 vs. CT-based Hounsfield Units (HU) in soft tissues, including cerebrospinal fluid (CSF), white matter (WM) and grey matter (GM).

By way of non-limiting example, a graph summarizing CT-measured Hounsfield unit (HU) values and corresponding MR-derived T1 values for a plurality of voxels with known tissue types are shown in FIG. 13A for bone tissue and in FIG. 13B for CSF, WM, and GM tissues. A correlation between R1 and CT HU was readily obtained from bone and all soft tissue classes, and distinct ranges of R1 values corresponding to each tissue type were readily identified. In one aspect, the ranges of T1 values associated with each tissue type as summarized in FIGS. 13A and 13B are used to define each tissue type's respective minimum and maximum values.

D) Assign HU Values to Plurality of Voxels in Region of Interest

Referring again to FIG. 1, each voxel of the plurality of voxels is assigned a CT Hounsfield Unit (HU) at 808. In another aspect, the HU that is assigned to each voxel is determined using a predetermined correlation between HU and one or more of the MRI parameters calculated at 804 and/or the tissue type assigned at 806. In various other aspects, predetermined multivariate relationships of CT HU vs. multiple MRI parameters including, but not limited to R1 and R2* are further derived and utilized to provide HU values for bone and other soft tissues.

In one aspect the HU assigned to each voxel is obtained from a predetermined correlation of CT Hounsfield unit (HU) with respect to the MRI parameter R1 (the inverse of T1). By way of non-limiting example, FIG. 13A is a graph summarizing a predetermined correlation of CT measured HU as a function of R1 for bone tissue that is used in the disclosed method to determine an HU to be assigned at 808 to bone tissue voxels. FIG. 13B is a graph summarizing predetermined correlations of CT measured HU as a function of R1 for cerebrospinal fluid (CSF), white matter (WM) and grey matter (GM) that are used in the disclosed method to determine an HU to be assigned at 808 to the corresponding voxels classified as these tissue types.

Figure 14:
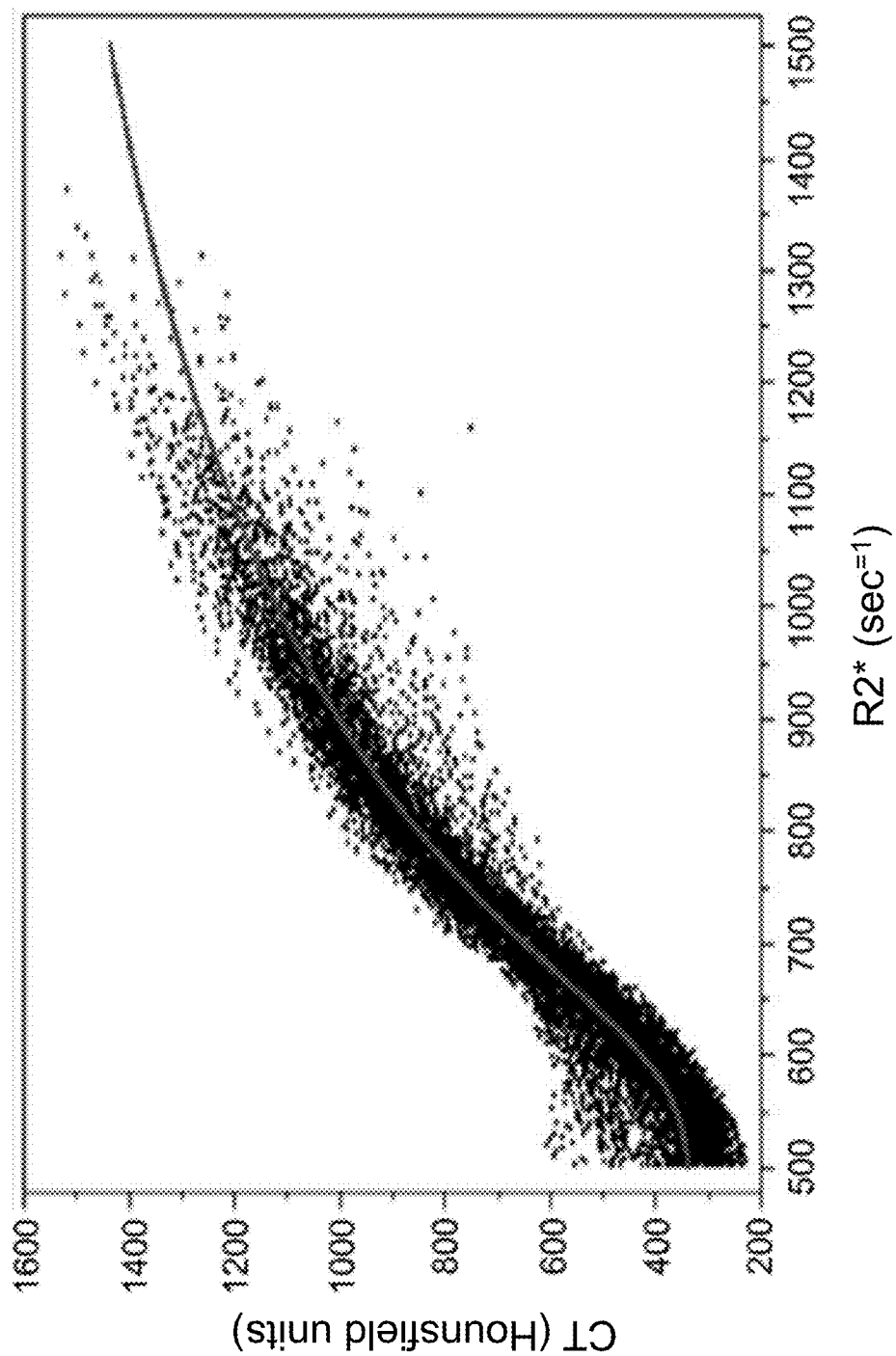
FIG. 14 is a graph of R2* vs. CT-based Hounsfield Unit (HU) in bone.

In another aspect, a predetermined correlation of CT-derived Hounsfield units (HU) with respect to the MRI parameter R2* is used to assign the HU to each voxel at 808. By way of non-limiting example, FIG. 14 is a graph summarizing a predetermined correlation of CT measured HU as a function of R2* for bone tissue used in another aspect to determine HU for voxels classified as bone.

In an aspect, the predetermined correlations between T1 and CT-Hounsfield unit (CT-HU) are produced by performing regression analysis according to known methods between CT-measured Hounsfield units (CT-HU) and MR-derived R1 values for a plurality of patients using data from voxels classified as bone, CSF, WM and GM by both modalities. In one aspect, voxel-by-voxel comparisons are used in the regression analysis for each tissue type. In another aspect, the voxel values are further processed to reduce the effect of random noise and/or other confounding factors on the resulting correlation. By way of non-limiting example, a spatially-mapped binning approach is used as part of the regression analysis. For each individual patient from whom imaging data is obtained, the R1 values of all voxels with the same assigned tissue type are sorted numerically and divided into 100 bins, each containing an equal number of voxels. For all voxels within an R1 bin, the CT-HU values are matched to the binned voxels through spatial correspondence from the registered CT image, and the mean R1 and CT-HU values of each bin is then fit to a suitable model including, but not limited to, a five-parameter sigmoid model as expressed in Equation (2):

$$CT = D + \frac{A-D}{\left[1+\left(\frac{T_1}{C}\right)^B\right]^G} \qquad \text{Equation (2)}$$

where: A=lower horizontal asymptote, B=steepness (positive), C=inflection point, D=higher horizontal asymptote, and G=asymmetry of steepness.

E) Produce Pseudo-CT Images and Related Maps

Referring again to FIG. 1, the method 800 of producing pseudo-CT images using DUFA-MUTE MR imaging includes producing the pseudo-CT image at 810. In one aspect, the plurality of voxels and corresponding HU assigned at 808 are combined to form the pseudo-CT image at 810

Referring again to FIG. 1, the method 800 of producing pseudo-CT images using DUFA-MUTE MR imaging optionally includes producing an attenuation map at 812. In one aspect, for each tissue type, a predetermined correlation between one of the MRI parameters, including, but not limited to R1 and an attenuation coefficient are assigned to each voxel. The plurality of voxels and corresponding attenuation coefficients are combined to form an attenuation map that includes the plurality of voxels within the region of interest as well as the attenuation coefficient assigned to each of the plurality of voxels. The attenuation map so formed is suitable for use in subsequent PET imaging data analysis. In various aspects, attenuation map produced at 812 of the method 800 enables the operation of a combined PET/MRI system.

Figure 15:
FIG. 15 contains images of R1 maps reconstructed from a four-minute DUFA-MUTE acquisition.

By way of non-limiting example, FIG. 15 includes images of the R1 maps, in which R1 is proportional to HU as described above. The MR signals were obtained from a 4-minute MR data acquisition from a pelvic region of a patient obtained using the DUFA-MUTE MRI sequence described above. As seen in FIG. 15, both the pelvic and femur bones are clearly identified in these R1 maps. Due to the presence of a wider variety of soft tissues in non-cranial regions of the body of a patient, R2* maps in body images do not typically distinguish bone from soft tissues including, but not limited to, muscles and other organs. In addition, there exists a higher degree of variation in density, morphology, and other characterizing features between skull and pelvic/femur bones. By way of another non-limiting example, FIG. 10 includes images of the R1 maps computed from a 3-minute MR data acquisition from a thorax region of a patient obtained using the DUFA-MUTE MRI sequence characterized by: TE1=0.07 ms, TE2=2.46 ms, TR=5 ms, FA1=3 degrees, and FA2=15 degrees. The disclosed method of producing pseudo-CT images of bone tissue using DUFA-MUTE MRI sequences overcomes many of the challenges of body MR imaging.

F) Produce Attenuation Map in Region of Interest

Referring again to FIG. 1, the method 800 optionally includes forming attenuation maps at 812. In various aspects, the attenuation maps include the plurality of voxels and associated linear attenuation coefficients (LACs) assigned to the plurality of voxels based on the pseudo-CT map produced at 810. In one aspect, the LACs are assigned to each voxel based on the tissue type assigned to each voxel at 806 and/or the value of one or more of the MRI parameters calculated at 804. In various aspects, the HU values derived from the predetermined correlations are utilized to provide continuous value linear attenuation coefficients (LAC) for bone and other soft tissues. In an aspect, the attenuation map formed at 812 is compatible with existing PET imaging methods and are used without significant modification. In another aspect, the attenuation maps are used as part of a combined PET/MRI system that obtains the attenuation map from MR image data according to the method described above.

Existing state-of-art CT-based methods provide continuous LAC values to accommodate the heterogeneity of tissues within an imaged region. Table 1 shows the typical ranges of LAC values in various types of tissue. Of note, depending on the density of bone, the LAC in bone shows the largest ranges of LAC values. However, the MR tissue segmentation based LACs assigns a single constant LAC value to each tissue type, leading to potentially large errors in PET imaging.

TABLE 1

LAC Ranges in Different Tissue Type or Compartment

| Tissue Compartment | LAC (cm$^{-1}$) |
| --- | --- |
| air | 0 |
| adipose | 0.086-0.093 |
| soft tissue | 0.094-0.100 |
| bone | 0.110-0.172 |

In various aspects, the CT HU values obtained using the predetermined correlations as described herein above are converted to continuous value LACs using any known method without limitation. In one aspect, the CT HU values are converted to LAC values using a piecewise linear scaling according to Equation (3) for HU<50 and Equation (4) for HU>50:

$$\mu=(9.6\times10^{-5})\cdot(HU+1000) \text{ cm}^{-1} \qquad \text{Equation (3)}$$

$$\mu=(5.1\times10^{-5})\cdot(HU+1000)+(4.71\times10^{-2}) \text{ cm}^{-1} \qquad \text{Equation (4)}$$

where $\mu$ is the linear attenuation coefficient and HU is the HU value assigned to each voxel as described herein above.

In various aspects, the suitable model fitted to the plotted CT-measured HU and the MRI parameter T1 values are used as a basis for a predetermined correlation in combination with known relationships between HU values and LAC values for bone, soft tissue and CSF. In another aspect, constant LAC values are assigned to voxels with tissue types for which no predetermined correlation with the MRI parameter T1 is available. In this other aspect, those voxels classified as air-containing are assigned a LAC value of 0 cm$^{-1}$, those voxels classified as fat-containing are assigned a LAC value of about 0.092 cm$^{-1}$.

Figure 16A:
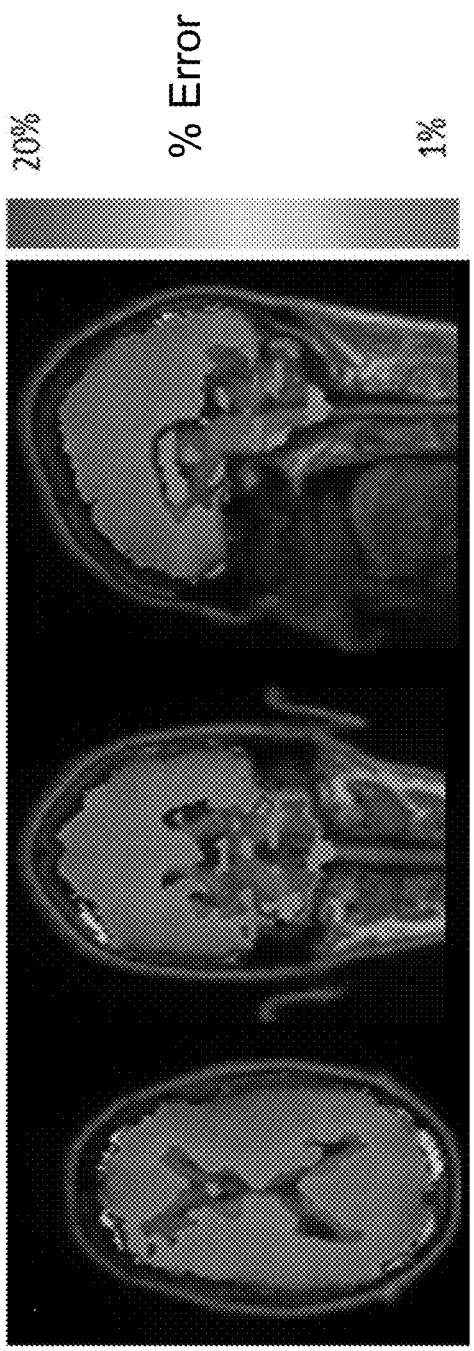
FIG. 16A is a map of the estimation error of attenuation coefficients (AC) for PET imaging displayed in the transverse, coronal, and sagittal planes. The error coefficients were obtained by comparing AC for PET imaging derived using DUFA-MUTE methods to a corresponding AC derived using analysis of computed tomography (CT) images.
Figure 16B:
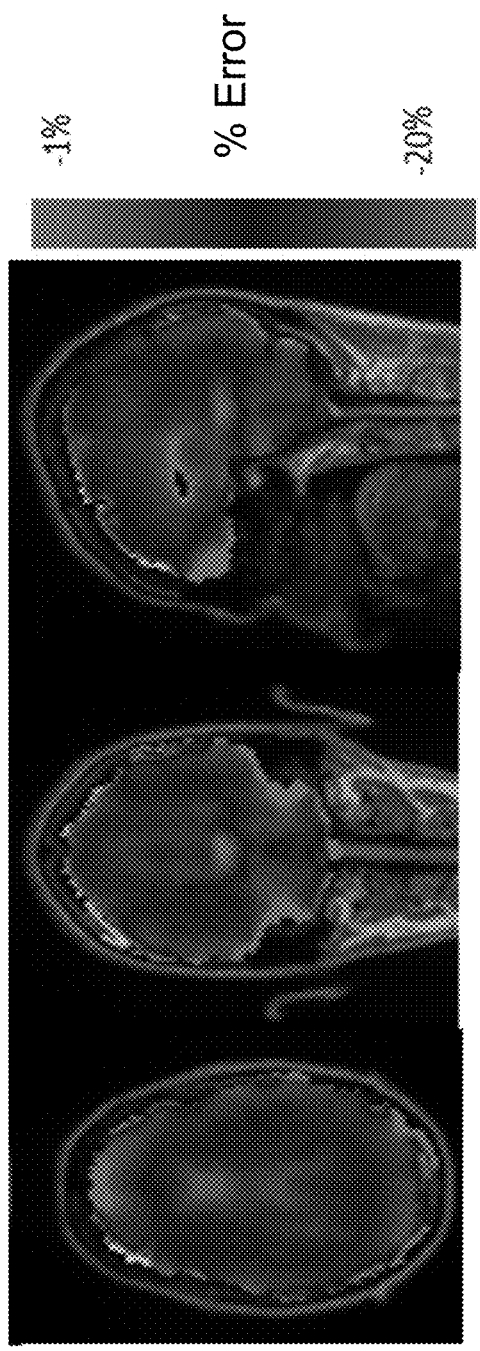
FIG. 16B is a map of the estimation error of attenuation coefficients (AC) for PET imaging displayed in the transverse, coronal, and sagittal planes. The error coefficients were obtained by comparing AC for PET imaging derived using a previous ultrashort echo time (UTE) method to a corresponding AC derived using analysis of computed tomography (CT) images.

By way of non-limiting example, the method described above was used to generate attenuation maps containing MR-derived continuous value LAC values (MRAC) for the tissue types identified within the head of a patient. Reconstructed PET using the DUFA-MUTE MR-derived MRAC values were compared to those using the well-accepted CT-derived attenuation coefficients (CTAC) to evaluate the accuracy of the DUFA-MUTE MRAC-derived PET images. Percent error maps (MRAC PET image values relative to CTAC PET images) were calculated on a voxel-by-voxel basis to evaluate the PET AC error resulting from the use of the MRAC in the PET imaging process. FIG. 16A shows representative percent error maps using the MRAC method described herein shown in the transverse, coronal, and sagittal views, characterized by a whole brain mean absolute percent error of 2.59±0.70%. FIG. 16B shows representative percent error maps using a previous MRAC method (Siemens' DUTE method) shown in the transverse, coronal, and sagittal views, characterized by a whole brain mean absolute percent error of 7.63±1.71%. The whole brain mean absolute percent error of the Siemens' DUTE method (FIG. 16B) was significantly higher than the corresponding whole brain mean absolute percent error of the DUFA-MUTE method (P<0.001).

G) Produce Electron Density Map in Region of Interest

The benefits of superior soft tissue contrast and a suite of anatomic, metabolic and physiological information have made MRI an excellent imaging modality in delineating lesions. However, a lack of electron density information in MR images presents a major challenge for accurate radiation dose calculation using MR images. Since CT HU can be directly converted to electron density, the current gold standard in radiation therapy planning is to fuse MR and CT images for the planning of radiation therapy treatment. However, patient body pose, as well as bladder and rectal filling, are quite different between CT and MR images. As a result, potentially substantial errors are introduced by fusing the CT and MR images.

Referring again to FIG. 1, the method 800 optionally includes producing electron density maps at 814. In various aspects, the electron density maps include the plurality of voxels and associated electron densities assigned to the plurality of voxels based on the pseudo-CT map produced at 810. In one aspect, the electron densities are assigned to each voxel based on the tissue type assigned to each voxel at 806 and/or the value of one or more of the MRI parameters calculated at 804. In various aspects, the HU values derived from predetermined correlations with respect to at least one MRI parameter are utilized to provide electron densities for bone and other soft tissues. In an aspect, the electron density map formed at 814 is compatible with existing treatment methods including, but not limited to, radiotherapy planning and administration and are used without significant modification. In another aspect, the electron density maps are used as part of an MRI-guided therapy system that obtains the electron density maps from MR image data according to the method described above.

II. MRI Systems

In various aspects, the DUFA-MUTE method for producing pseudo-CT images of bone tissue using DUFA-MUTE MR imaging described above are incorporated into any suitable MRI or combined PET/MRI system to enable MR imaging of bone tissue and/or combined PET/MR imaging on a patient.

Figure 17:
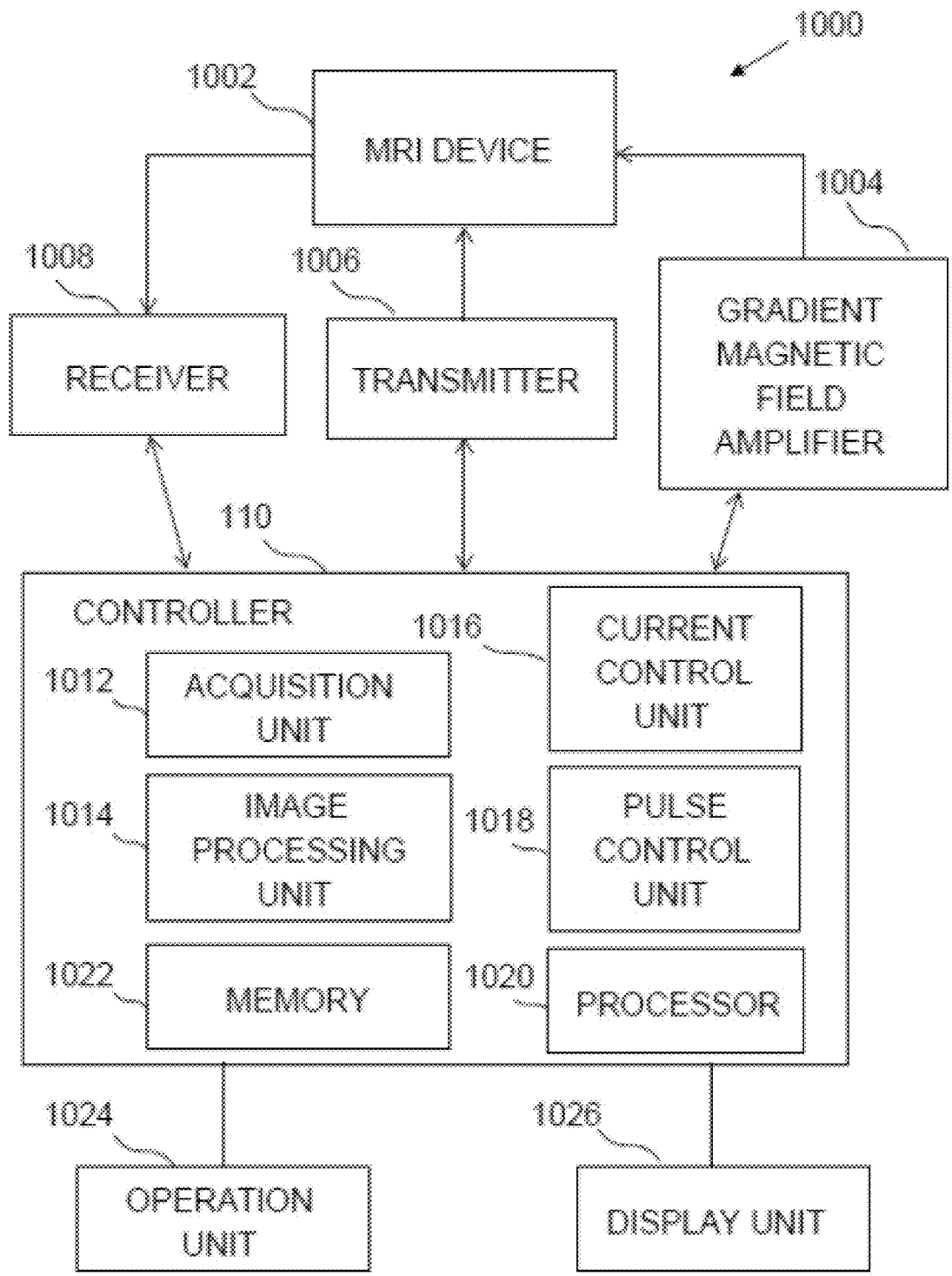
FIG. 17 is a block diagram illustrating elements of an MRI system for obtaining a pseudo-CT image using DUFA-MUTE MR imaging data in one aspect.

FIG. 17 is a block diagram of a simplified MRI system 900 in one aspect. The MRI system 1000 includes an MRI device 1002, a gradient magnetic field amplifier 1004, a transmitter 1006, a receiver 1008, and a controller 1010. In some aspects, the components of the MRI system 1000 are combined and/or separated in alternative arrangements. In other aspects, the MRI system 1000 includes additional elements configured to provide support and/or additional capabilities for the elements of the MRI system 1000 shown in FIG. 17.

Referring again to FIG. 17, the MRI scanner 1002 includes at least one magnet (not shown) coupled to a plurality of coils (not shown). In an aspect, the MRI scanner 1002 includes one magnet with a bore to house a patient (not shown). In some aspects, in which the MRI scanner 1002 includes at least two magnets, the patient is positioned between at least one pair of magnets. In various aspects, the coils include a superconductive coil configured to produce a static magnetic field, an RF coil configured to produce an RF pulse, three gradient coils configured to produce a gradient magnetic field along each axis of the x-y-z grid, and a receiving coil (not shown) configured to capture the output MR signals of the MRI scanner 1002. The gradient magnetic fields are adjustable to collect output signals for a particular direction or angle relative to the x-y-z axes.

The gradient magnetic field amplifier 1004 is configured to couple to each gradient coil of the MRI scanner 1002. The gradient magnetic field amplifier 1004 is configured to output an amplified gradient magnetic field signal to the gradient coils to induce the gradient magnetic fields. The transmitter 1006 is configured to couple to the RF coil to supply current to the RF coil of the MRI scanner 1002 to generate RF pulses.

The receiver 1008 is configured to couple to the receiving coil to process the output signal of the MRI scanner 1002. In an aspect, the receiver 1008 is configured to periodically capture the output signal to be sent to the controller 1010 for image processing. In other aspects, the receiver 1008 is configured to capture the output signal in response to a trigger and/or a signal from controller 1010.

The controller 1010 is configured to communicate with the gradient magnetic field amplifier 1004, the transmitter 1006, and the receiver 1008 to send and receive data (e.g., image data) and control information (e.g., current monitoring). In some aspects, the controller 1010 is configured to communicate with the MRI scanner 1002 to monitor and/or to control the operation of the MRI scanner 1002.

The controller 1010 includes an acquisition unit 1012, an image processing unit 1014, a current control unit 1016, a pulse control unit 1018, at least one processor 1020, and a memory 1022. In the example aspect, the controller 1010 is a computing device further including an operation unit 1024 and a display unit 1026. The at least one processor of the controller 1010 includes the image processing unit 1014, the acquisition unit 1012, the current control unit 1016, and/or the pulse control unit 1018.

The acquisition unit 1012 is configured to control the gradient magnetic field amplifier 1004 to adjust a direction or orientation of the output signal collected by the MRI scanner 1002. More specifically, the acquisition unit 1012 is configured to control the gradient magnetic field amplifier based on a DUFA-MUTE MRI sequence described herein previously. In at least some aspects, the acquisition unit 1012 is configured to receive the output signals for analysis prior to transmitting the output signals to the image processing unit 1014. In other aspects, the acquisition unit 1012 is configured to transmit acquisition data associated with the output signals to the image processing unit 1014.

The image processing unit 1014 is configured to receive the output signal to produce an image to be displayed. In one aspect, the image processing unit 1014 is configured to process the MR output signal data to form a parametric map, assign a tissue type to each voxel, assign a linear attenuation coefficient to each voxel, and to form an attenuation map as described herein above. In another aspect, the image processing unit 1014 is configured to process the MR output signal data to assign a tissue type to each voxel, assign an HU value to each voxel, and to generate CT-type image data as described herein above. In yet another aspect, the image processing unit 1014 is configured to transfer an attenuation map produced by the image processing unit 1014 to a PET imaging device (not shown) operatively coupled to system 1000 or integrated into the system 1000.

The current control unit 1016 is configured to regulate the input current of the gradient magnetic field amplifier 1004 and the transmitter 1006 to facilitate currents within the current ratings of each component. In some aspects, the current control unit is configured to monitor electric current data received from the MRI system 1000.

The pulse control unit 1018 is configured to communicate with the transmitter 1006 to generate RF pulses within the MRI scanner 1002 to create the output signal received by the receiver 1008. In some aspects, the pulse control unit 1018 is configured to communicate with the gradient magnetic field amplifier 1004 to monitor and/or control the gradient magnetic field signals sent to the MRI scanner 1002.

Processor 1020 includes any type of conventional processor, microprocessor, or processing logic that interprets and executes instructions. Processor 1020 is configured to process instructions for execution within the controller 1010, including instructions stored in the memory 1022 to display graphical information for a GUI on an external input/output device, such as display 1026 coupled to a high speed interface. In other implementations, multiple processors and/or multiple buses are used, as appropriate, along with multiple memories and types of memory. Also, multiple controllers 1010 are connected, with each device providing portions of the necessary operations (e.g., as a server bank, a group of blade servers, or a multi-processor system). In some aspects, the processor 1020 includes the acquisition unit 1012, the image processing unit 1014, the current control unit 1016, and/or the pulse control unit 1018.

The memory 1022 facilitates data storage in the MRI system 1000. In some aspects, the memory 1022 includes a plurality of storage components such as, but not limited to, a hard disk drive, flash memory, random access memory, and a magnetic or optical disk. Alternatively or additionally, the memory 1022 includes remote storage such a server in communication with the controller 1010. The memory 1022 stores at least one computer program that, when received by the at least one processor, cause the at least one processor to perform any of the functions of the controller 1010 described above. In one implementation, the memory 1022 are or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product also contains instructions that, when executed, perform one or more functions, such as those described herein. The information carrier is a non-transitory computer- or machine-readable medium, such as the memory 1022 or memory on the processor 1020. Additionally, the memory 1022 is configured to facilitate storage of a plurality of images obtained by the MRI scanner 1002 as processed by the controller 1010.

The operation unit 1024 are configured to enable a user to interface (e.g., visual, audio, touch, button presses, stylus taps, etc.) with the controller 1010 to control the operation of the MRI system 1000. In some aspects, the operation unit 1024 is further coupled to the MRI scanner 1002 to control the operation of the MRI scanner 1002.

The display unit 1026 enables a user to view data and control information of the MRI system 1000. The display unit 1026 is further coupled to other components of the MRI system 1000 such as the MRI scanner 1002. The display unit 1026 includes a visual display such as a cathode ray tube (CRT) display, liquid crystal display (LCD), light emitting diode (LED) display, or "electronic ink" display. In some aspects, the display unit 1026 is configured to present a graphical user interface (e.g., a web browser and/or a client application) to the user. A graphical user interface includes, for example, an image display for images acquired by the MRI system 1000 of a patient, operational data of the MRI system 1000, and the patient's physiological data (e.g., heart rate).

As used herein, a processor such as the processor 1020 includes any programmable system including systems using micro-controllers, reduced instruction set circuits (RISC), application specific integrated circuits (ASICs), logic circuits, and any other circuit or processor capable of executing the functions described herein. The above examples are example only, and are thus not intended to limit in any way the definition and/or meaning of the term "processor."

Figure 18:
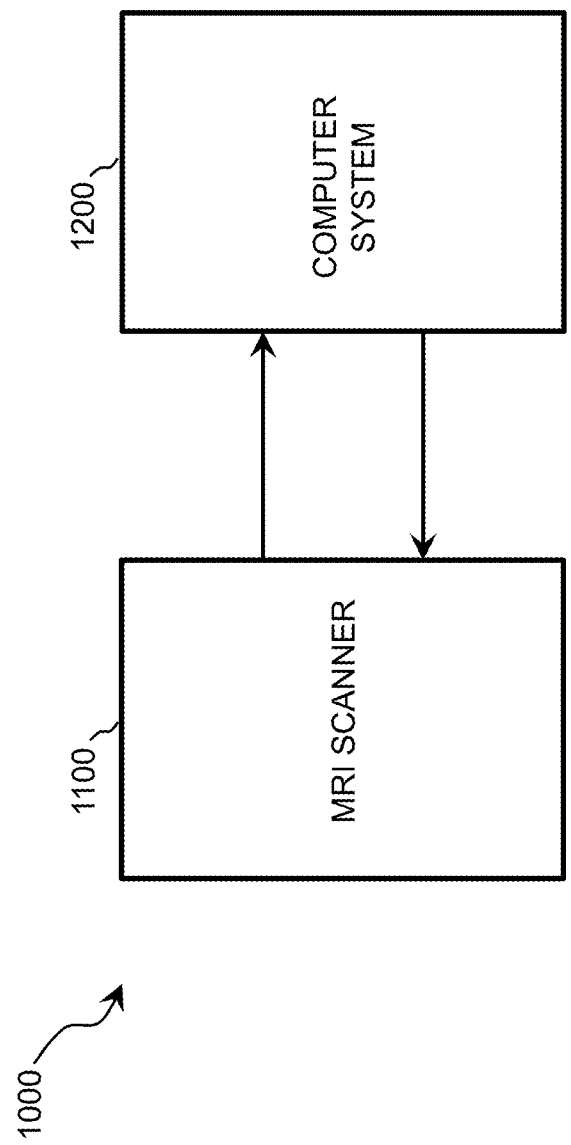
FIG. 18 is a schematic block diagram of an MRI imaging system in one aspect.

FIG. 18 is a block diagram of a DUFA-MUTE MRI system 1000 in another aspect. In this other aspect, the DUFA-MUTE MRI system 1000 includes an MRI scanner 1100, and a computing device 1200 operatively coupled to the MRI scanner.

Figure 19:
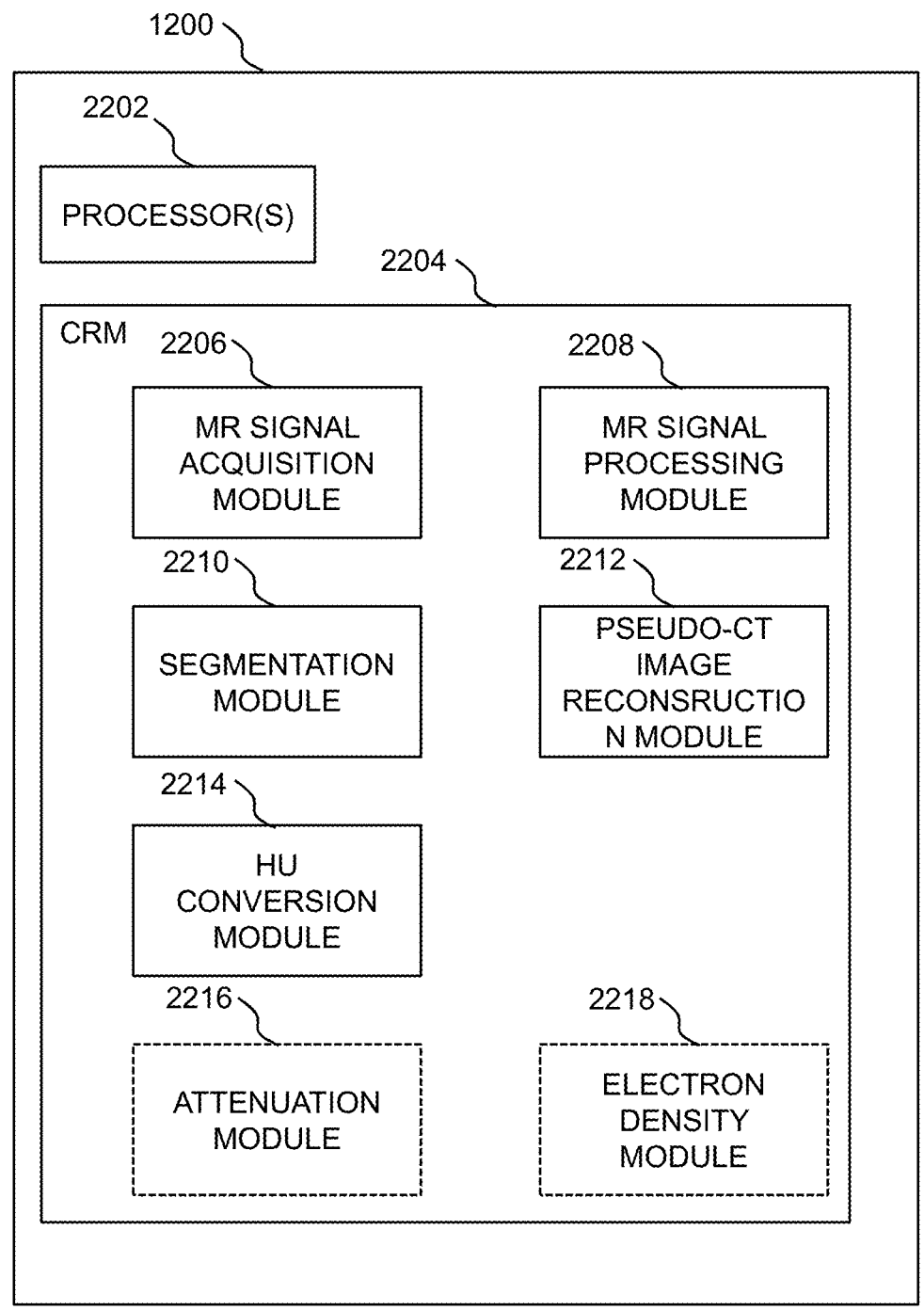
FIG. 19 is a block diagram illustrating the elements of a computing device of a DUFA-MUTE MRI system according to one aspect of the disclosed method.

FIG. 19 is a block diagram illustrating the elements of a computing device 1200 of a DUFA-MUTE MRI system 1000 in another aspect. In this other aspect, the computing device includes at least one processor 2202 and a computer-readable media 2204. The computer-readable media encodes a plurality of modules, each module of the plurality of modules comprising a plurality of instructions executable by the at least one processor 2202. The plurality of modules include an MR signal acquisition module 2206 configured to operate the MRI scanner (not illustrated) according to a DUFA-MUTE MRI sequence as described above and to receive a plurality of MR signals associated with a plurality of voxels within the at least a portion of the patient.

Referring again to FIG. 19, the CRM 2204 further includes an MR signal processing module 2208 configured to calculate at least one MRI parameter for each voxel of the plurality of voxels based on a portion of the plurality of MR signals associated with that voxel, in which the at least one MRI parameter includes R1 according to the methods described above. The CRM 2204 further includes a segmentation module 2210 configured to assign a tissue type to each voxel based on at least a portion of the at least one MRI parameter associated with that voxel according to a plurality of tissue assignment criteria according to the methods described above. The CRM 2204 additionally includes a Hounsfield unit conversion module 2214 configured to assign an HU value to each voxel based on the assigned tissue type and the at least one MR parameter associated with that voxel according to the methods described above. The CRM 2204 further additionally includes a pseudo-CT image reconstruction module 2212 configured to produce the pseudo-CT image comprising a map of the plurality of voxels and associated HU values according to the methods described above.

In one additional aspect, the CRM 2204 optionally includes an attenuation module configured to assign LAC values to the plurality of voxels and to produce an attenuation map based on a pseudo-CT map according to the methods described above. In a second additional aspect, the CRM 2204 optionally includes an electron density module 2218 configured to assign electron density values to the plurality of voxels and to produce an electron density map based on a pseudo-CT map according to the methods described above.

In one aspect, the DUFA-MUTE method for producing an attenuation map for combined PET/MR imaging and/or the method for obtaining CT-like images of bone tissue using DUFA-MUTE MR imaging are incorporated into any known suitable MRI system without limitation. In one non-limiting example, the MRI system is an MRI system that includes an MRI scanner, a receiver, and a controller for operating and monitoring the elements of the MRI scanner. Typically, the MRI scanner are configured to output a radio frequency (RF) signal to the receiver that, when processed by the controller, are used to generate image data to be displayed to a user. In this example, the MRI system is configured to acquire and display MR imaging data of bone tissue obtained from the cranium and/or body of a patient. In another aspect, the controller are further configured to process the MR imaging data as described herein above to produce an attenuation map suitable for use in PET imaging. In yet another aspect, the MRI system are operatively coupled to a PET system to perform combined PET/MR imaging using an attenuation map obtained using the DUFA-MUTE MRI method described herein above.

As described herein, computing devices and computer systems include a processor and a memory. However, any processor in a computer device referred to herein also refers to one or more processors wherein the processor are in one computing device or a plurality of computing devices acting in parallel. Additionally, any memory in a computer device referred to herein also refers to one or more memories wherein the memories are in one computing device or a plurality of computing devices acting in parallel.

Although the present invention is described in connection with an exemplary imaging system environment, aspects of the invention are operational with numerous other general purpose or special purpose imaging system environments or configurations. The imaging system environment is not intended to suggest any limitation as to the scope of use or functionality of any aspect of the invention. Moreover, the imaging system environment should not be interpreted as having any dependency or requirement relating to any one or combination of components illustrated in the exemplary operating environment. Examples of well-known imaging systems, environments, and/or configurations that are suitable for use with aspects of the invention include, but are not limited to, personal computers, server computers, hand-held or laptop devices, multiprocessor systems, microprocessor-based systems, set top boxes, programmable consumer electronics, mobile telephones, network PCs, minicomputers, mainframe computers, distributed computing environments that include any of the above systems or devices, and the like.

Computer systems, as described herein, refer to any known computing device and computer system. As described herein, all such computer systems include a processor and a memory. However, any processor in a computer system referred to herein also refers to one or more processors wherein the processor are in one computing device or a plurality of computing devices acting in parallel. Additionally, any memory in a computer device referred to herein also refers to one or more memories wherein the memories are in one computing device or a plurality of computing devices acting in parallel.

The term processor, as used herein, refers to central processing units, microprocessors, microcontrollers, reduced instruction set circuits (RISC), application specific integrated circuits (ASIC), logic circuits, and any other circuit or processor capable of executing the functions described herein. The above are examples only, and are thus not intended to limit in any way the definition and/or meaning of the term "processor."

As used herein, the term "database" refers to either a body of data, a relational database management system (RDBMS), or to both. As used herein, a database includes any collection of data including hierarchical databases, relational databases, flat file databases, object-relational databases, object-oriented databases, and any other structured collection of records or data that is stored in a computer system. The above examples are example only, and thus are not intended to limit in any way the definition and/or meaning of the term database. Examples of RDBMSs include, but are not limited to including, Oracle® Database, MySQL, IBM® DB2, Microsoft® SQL Server, Sybase®, and PostgreSQL. However, any database are used that enables the systems and methods described herein. (Oracle is a registered trademark of Oracle Corporation, Redwood Shores, Calif.; IBM is a registered trademark of International Business Machines Corporation, Armonk, N.Y.; Microsoft is a registered trademark of Microsoft Corporation, Redmond, Wash.; and Sybase is a registered trademark of Sybase, Dublin, Calif.)

In one aspect, a computer program is provided to enable the data processing of the DUFA-MUTE MRI method as described herein above, and this program is embodied on a computer readable medium. In an example aspect, the computer system is executed on a single computer system, without requiring a connection to a server computer. In a further aspect, the computer system is run in a Windows® environment (Windows is a registered trademark of Microsoft Corporation, Redmond, Wash.). In yet another aspect, the computer system is run on a mainframe environment and a UNIX® server environment (UNIX is a registered trademark of X/Open Company Limited located in Reading, Berkshire, United Kingdom). Alternatively, the computer system is run in any suitable operating system environment. The computer program is flexible and designed to run in different environments without compromising any major functionality. In some aspects, the computer system includes multiple components distributed among a plurality of computing devices. One or more components are in the form of computer-executable instructions embodied in a computer-readable medium.

The computer systems and processes are not limited to the specific aspects described herein. In addition, components of each computer system and each process can be practiced independent and separate from other components and processes described herein. Each component and process also can be used in combination with other assembly packages and processes.

Figure 20:
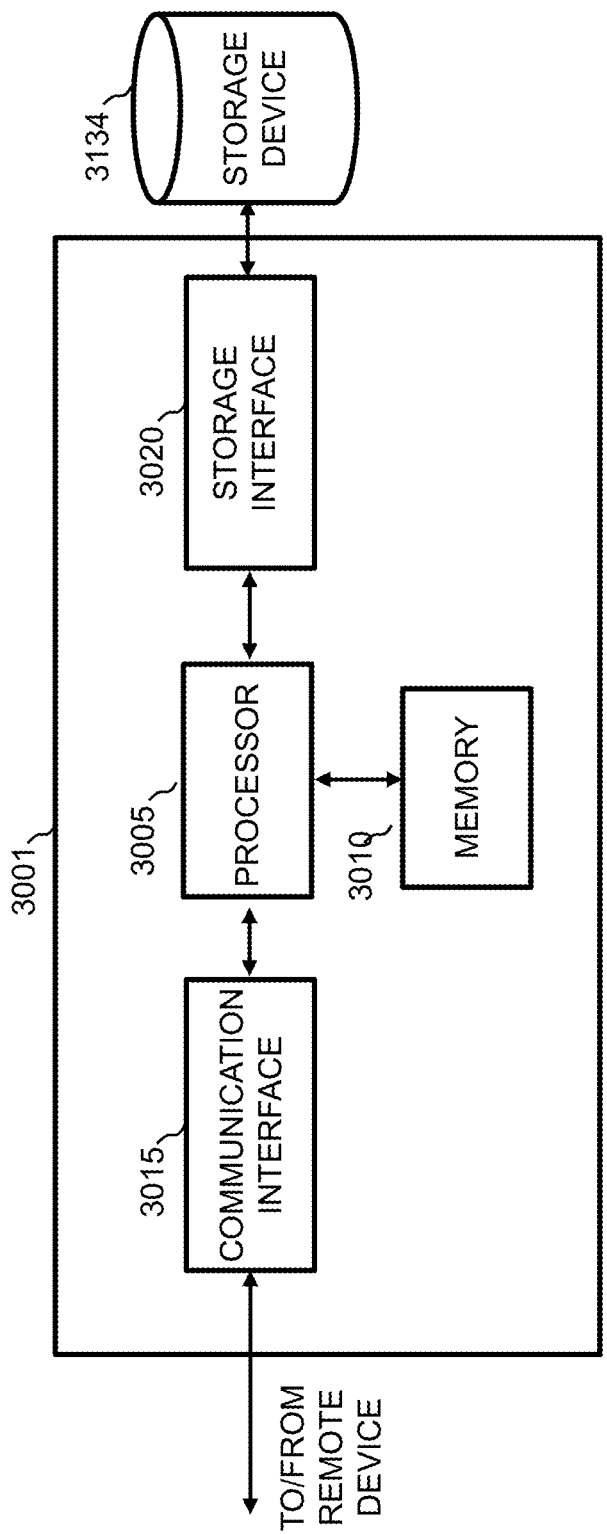
FIG. 20 is a schematic block diagram of an example server system.

In one aspect, the computer system is configured as a server system. FIG. 20 illustrates an example configuration of a server system 3001 used to receive measurements from the MRI scanner 1100 (not illustrated). Referring again to FIG. 20, server system 3001 also includes, but is not limited to, a database server. In this example aspect, server system 3001 performs all of the steps used to implement the MRI imaging method as described herein above.

In this aspect, the server system 3001 includes a processor 3005 for executing instructions. Instructions are stored in a memory area 3010, for example. The processor 3005 includes one or more processing units (e.g., in a multi-core configuration) for executing instructions. The instructions are executed within a variety of different operating systems on the server system 3001, such as UNIX, LINUX, Microsoft Windows®, etc. It should also be appreciated that upon initiation of a computer-based method, various instructions are executed during initialization. Some operations are required in order to perform one or more processes described herein, while other operations are more general and/or specific to a particular programming language (e.g., C, C #, C++, Java, or any other suitable programming languages).

The processor 3005 is operatively coupled to a communication interface 3015 such that server system 3001 is capable of communicating with a remote device, such as the MRI scanner 1100, a user system, or another server system 301. For example, communication interface 3015 receives requests (e.g., requests to provide an interactive user interface to receive sensor inputs and to control one or more devices of system 1000 from a client system via the Internet.

Processor 3005 is also operatively coupled to a storage device 3134. Storage device 3134 is any computer-operated hardware suitable for storing and/or retrieving data. In some aspects, storage device 3134 is integrated in server system 3001. For example, server system 3001 includes one or more hard disk drives as storage device 3134. In other aspects, storage device 3134 is external to server system 3001 and is accessed by a plurality of server systems 3001. For example, storage device 3134 includes multiple storage units such as hard disks or solid-state disks in a redundant array of inexpensive disks (RAID) configuration. Storage device 3134 includes a storage area network (SAN) and/or a network attached storage (NAS) system.

In some aspects, processor 3005 is operatively coupled to storage device 3134 via a storage interface 3020. Storage interface 3020 is any component capable of providing processor 3005 with access to storage device 3134. Storage interface 3020 includes, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 3005 with access to storage device 3134.

Memory area 3010 includes, but is not limited to, random access memory (RAM) such as dynamic RAM (DRAM) or static RAM (SRAM), read-only memory (ROM), erasable programmable read-only memory (EPROM), electrically erasable programmable read-only memory (EEPROM), non-volatile RAM (NVRAM), registers, hard disk memory, a removable disk, a CD-ROM, or any other form of computer-readable storage medium known in the art. The above memory types are exemplary only, and are thus not limiting as to the types of memory usable for storage of a computer program.

Figure 21:
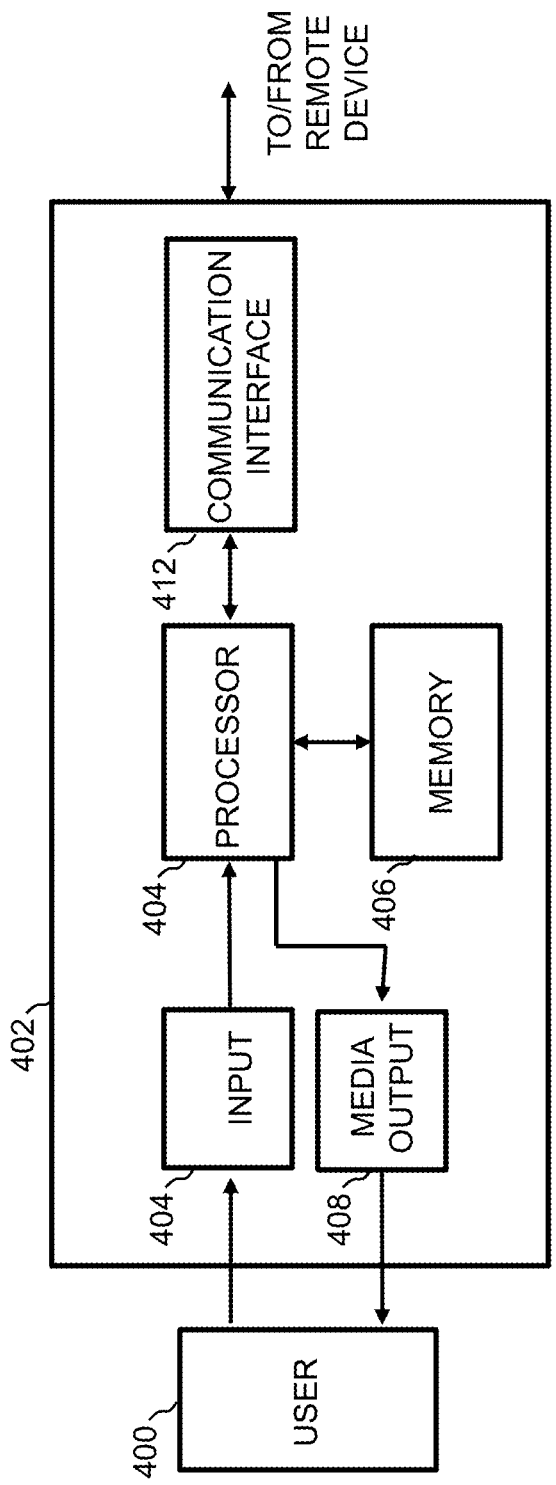
FIG. 21 is a block diagram of an example computing device.

In another aspect, the computer system is provided in the form of a computing device, such as a computing device 402 (shown in FIG. 21). Computing device 402 includes a processor 404 for executing instructions. In some aspects, executable instructions are stored in a memory area 406. Processor 404 includes one or more processing units (e.g., in a multi-core configuration). Memory area 406 is any device allowing information such as executable instructions and/or other data to be stored and retrieved. Memory area 406 includes one or more computer-readable media.

In another aspect, the memory included in the computing device 402 includes a plurality of modules. Each module includes instructions configured to execute using at least one processor. The instructions contained in the plurality of modules implement at least part of the method for simultaneously regulating a plurality of process parameters as described herein when executed by the one or more processors of the computing device. Non-limiting examples of modules stored in the memory of the computing device include: a first module to receive measurements from one or more sensors and a second module to control one or more devices of the MRI imaging system 1000.

Computing device 402 also includes one media output component 408 for presenting information to a user 400. Media output component 408 is any component capable of conveying information to user 400. In some aspects, media output component 408 includes an output adapter such as a video adapter and/or an audio adapter. An output adapter is operatively coupled to processor 404 and is further configured to be operatively coupled to an output device such as a display device (e.g., a liquid crystal display (LCD), organic light emitting diode (OLED) display, cathode ray tube (CRT), or "electronic ink" display) or an audio output device (e.g., a speaker or headphones).

In some aspects, client computing device 402 includes an input device 410 for receiving input from user 400. Input device 410 includes, for example, a keyboard, a pointing device, a mouse, a stylus, a touch sensitive panel (e.g., a touch pad or a touch screen), a camera, a gyroscope, an accelerometer, a position detector, and/or an audio input device. In one aspect, a single component such as a touch screen functions as both an output device of media output component 408 and input device 410.

In another aspect, the computing device 402 also includes a communication interface 412, which is configured to communicatively couple to a remote device such as server system 302 or a web server. Communication interface 412 includes, for example, a wired or wireless network adapter or a wireless data transceiver for use with a mobile phone network (e.g., Global System for Mobile communications (GSM), 3G, 4G or Bluetooth) or other mobile data network (e.g., Worldwide Interoperability for Microwave Access (WIMAX)).

Stored in memory area 406 are, for example, computer-readable instructions for providing a user interface to user 400 via media output component 408 and, optionally, receiving and processing input from input device 410. A user interface includes, among other possibilities, a web browser and an application. Web browsers enable users 400 to display and interact with media and other information typically embedded on a web page or a website from a web server. An application allows users 400 to interact with a server application.

Exemplary aspects of methods, systems, and apparatus for use in DUFA-MUTE MR imaging are described above in detail. The methods, systems, and apparatus are not limited to the specific aspects described herein but, rather, operations of the methods and/or components of the systems and/or apparatus are utilized independently and separately from other operations and/or components described herein. Further, the described operations and/or components may also be defined in, or used in combination with, other systems, methods, and/or apparatus, and are not limited to practice with only the systems, methods, and apparatus described herein.

The order of execution or performance of the operations in the aspects of the invention illustrated and described herein is not essential, unless otherwise specified. That is, the operations are performed in any order, unless otherwise specified, and aspects of the invention include additional or fewer operations than those disclosed herein. For example, it is contemplated that executing or performing a particular operation before, contemporaneously with, or after another operation is within the scope of aspects of the invention.

It will be understood by those of skill in the art that information and signals are represented using any of a variety of different technologies and techniques. For example, data, instructions, commands, information, signals, bits, symbols, and/or chips are represented by voltages, currents, electromagnetic waves, magnetic fields or particles, optical fields or particles, or any combination thereof. Similarly, the various illustrative logical blocks, modules, circuits, and algorithm operations described herein are implemented as electronic hardware, computer software, or a combination of both, depending on the application and the functionality. Moreover, the various logical blocks, modules, and circuits described herein are implemented or performed with a general purpose computer, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. Exemplary general-purpose processors include, but are not limited to only including, microprocessors, conventional processors, controllers, microcontrollers, state machines, or a combination of computing devices.

When introducing elements of aspects of the invention or aspects thereof, the articles "a," "an," "the," and "said" are intended to mean that there are one or more of the elements. The terms "comprising," "including," and "having" are intended to be inclusive and mean that there are additional elements other than the listed elements.

This written description uses examples to disclose the invention, including the best mode, and also to enable any person skilled in the art to practice the invention, including making and using any devices or systems and performing any incorporated methods. The patentable scope of the invention is defined by the claims, and includes other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A DUFA-MUTE MRI system configured to obtain a pseudo-CT image of at least a portion of a patient, the system comprising:
    an MRI scanner;
    a computing device operatively coupled to the MM scanner, the computing device comprising at least one processor and a computer-readable media, the computer-readable media encoding a plurality of modules, each module of the plurality of modules comprising a plurality of instructions executable by the at least one processor, the plurality of modules comprising:
        an MR signal acquisition module configured to operate an MM scanner according to a DUFA-MUTE MRI sequence and to receive a plurality of MR signals associated with a plurality of voxels within the at least a portion of the patient;
        an MR signal processing module configured to calculate at least one MM parameter for each voxel of the plurality of voxels based on a portion of the plurality of MR signals associated with that voxel, the at least one MRI parameter comprising R1;
        a segmentation module configured to assign a tissue type to each voxel based on at least a portion of the at least one MM parameter associated with that voxel according to a plurality of tissue assignment criteria;
        a Hounsfield unit conversion module configured to assign an HU value to each voxel based on the assigned tissue type and the at least one MM parameter associated with that voxel; and
        a pseudo-CT image reconstruction module configured to produce the pseudo-CT image comprising a map of the plurality of voxels and associated HU values, wherein:
            the DUFA-MUTE MRI sequence comprises a first multiple ultrashort echo time sequence characterized by a first flip angle FA1, a first echo time TE1 and a second echo time TE2, and further comprises a second multiple ultrashort echo time sequence characterized by a second flip angle FA2, the first echo time TE1 and the second echo time TE2;
            the first flip angle FA1 is selected to enhance a magnitude of MR signals from cerebrospinal fluid;
            the second flip angle FA2 is selected to enhance a magnitude of MR signals from bone measured at the first echo time TE1;
            the first echo time TE1 is further selected to obtain in-phase MR signals from water and fat at the first flip angle FA1; and
            the second echo time TE2 is selected to attenuate a magnitude of MR signals from bone and is further selected to obtain out-of-phase water and fat signals at the first flip angle FA1.

2. The system of claim 1, wherein the first multiple ultrashort echo time sequence and the second multiple ultrashort echo time sequence of the DUFA-MUTE MM sequence further comprises at least one additional echo time.

3. The system of claim 1, wherein the plurality of tissue assignment criteria comprises:
    assigning a tissue type of bone to each voxel with an R1 value of greater than a minimum R1 bone bound;
    assigning a tissue type of grey matter to each voxel with an R1 value ranging from a minimum GM bound to a maximum GM bound;
    assigning a tissue type of white matter to each voxel with an R1 value ranging from a minimum WM bound to a maximum WM bound; and
    assigning a tissue type of cerebrospinal fluid to each voxel with an R1 value ranging from a minimum CSF bound to a maximum CSF bound.

4. The system of claim 3, wherein the minimum R1 bone bound is about 5 $ms^{-1}$, the minimum GM bound is about 2.5 $ms^{-1}$, the maximum GM bound is about 5 $ms^{-1}$, the minimum WM bound is about 1 $ms^{-1}$, the maximum WM bound is about 2.5 $ms^{-1}$, the minimum CSF bound is 0 $ms^{-1}$, and the maximum CSF bound is about 1 $ms^{-1}$.

5. The system of claim 4, wherein the at least one MRI parameter further comprises at least one additional MRI parameter selected from the group consisting of $R2^*$, $iUTE_{FA1}$, $iUTE_{FA2}$, $WATER_{FA1}$, and $FAT_{FA1}$.

6. The system of claim 5, wherein the plurality of tissue assignment criteria further comprises:
    assigning a tissue type of air to each voxel with a normalized $iUTE_{FA1}$ value of greater than a minimum air bound;
    assigning a tissue type of bone to each voxel with an $R2^*$ value of greater than a minimum $R2^*$ bone bound;

assigning a tissue type of fat to each voxel with an associated $\text{FAT}_{FA1}$ value greater than a minimum fat bound;

assigning a tissue type of soft tissue to each voxel with an associated $\text{WATER}_{FA1}$ greater than a minimum soft tissue bound; and assigning a tissue type of soft tissue to each voxel not assigned a tissue type according to any preceding tissue assignment criterion of the plurality of tissue assignment criteria.

7. The system of claim 6, wherein the minimum air bound is about 0.06, the minimum R2* bone bound is about 550 s$^{-1}$, the minimum fat bound is about 250, and the minimum soft tissue bound is about 150.

8. The system of claim 1, wherein the plurality of modules further comprises an attenuation module configured to assign a linear attenuation coefficient value μ to each voxel based on the HU value associated with that voxel.

9. The system of claim 8, wherein the linear attenuation coefficient value μ is calculated according to a conversion equation of the group of conversion equations consisting of:

$$\mu=(9.6\times10^{-5})\cdot(\text{HU}+1000) \text{ cm}^{-1} \text{ for HU}<50; \text{ and}$$

$$\mu=(5.1\times10^{-5})\cdot(\text{HU}+1000)+(4.71\times10^{-2}) \text{ cm}^{-1} \text{ for HU}<50.$$

10. The system of claim 8, wherein the attenuation module is configured to assign the linear attenuation coefficient value μ to each voxel based on the assigned tissue type and the at least one MM parameter associated with that voxel.

11. The system of claim 1, wherein the plurality of modules further comprises an electron density module configured to assign an electron density value to each voxel based on the HU value associated with that voxel.

12. The system of claim 11, wherein the electron density module is configured to assign the electron density value to each voxel based on the assigned tissue type and the at least one MRI parameter associated with that voxel.

13. A method for obtaining a pseudo-CT image of at least a portion of a patient, the method comprising:

obtaining a plurality of MR signals from a plurality of voxels within the at least a portion of the patient according to a DUFA-MUTE MRI sequence, the DUFA-MUTE MRI sequence comprising a first multiple ultrashort echo time sequence characterized by a first flip angle FA1, a first echo time TE1 and a second echo time TE2, and further comprising a second multiple ultrashort echo time sequence characterized by a second flip angle FA2, the first echo time TE1 and the second echo time TE2;

calculating at least one MM parameter for each voxel of the plurality of voxels based on a portion of the plurality of MR signals associated with that voxel, the at least one MM parameter comprising R1;

assigning a tissue type to each voxel based on at least a portion of the at least one MRI parameter associated with that voxel according to a plurality of tissue assignment criteria;

assigning an HU value to each voxel based on the assigned tissue type and the at least one MRI parameter associated with that voxel; and producing the pseudo-CT image comprising a map of the plurality of voxels and associated HU values, wherein obtaining the plurality of MR signals from the plurality of voxels within the at least a portion of the patient according to the DUFA-MUTE MRI sequence, further includes:

selecting the first flip angle FA1 to enhance a magnitude of MR signals from cerebrospinal fluid;

selecting the second flip angle FA2 to enhance a magnitude of MR signals from bone measured at the first echo time TE1;

selecting the first echo time TE1 to obtain in-phase MR signals from water and fat at the first flip angle FA1; and selecting the second echo time TE2 to attenuate a magnitude of MR signals from bone and further to obtain out-of-phase water and fat signals at the first flip angle FA1.

14. The method of claim 13, wherein the first multiple ultrashort echo time sequence and the second multiple ultrashort echo time sequence of the DUFA-MUTE MRI sequence further comprises at least one additional echo time.

15. The method of claim 13, wherein assigning the tissue type to each voxel based on at least a portion of the at least one MRI parameter associated with that voxel according to the plurality of tissue assignment criteria further comprises:

assigning a tissue type of bone to each voxel with an R1 value of greater than a minimum R1 bone bound;

assigning a tissue type of grey matter to each voxel with an R1 value ranging from a minimum GM bound to a maximum GM bound;

assigning a tissue type of white matter to each voxel with an R1 value ranging from a minimum WM bound to a maximum WM bound; and assigning a tissue type of cerebrospinal fluid to each voxel with an R1 value ranging from a minimum CSF bound to a maximum CSF bound.

16. The method of claim 15, wherein assigning the tissue type to each voxel based on at least a portion of the at least one MRI parameter associated with that voxel according to the plurality of tissue assignment criteria further comprises defining the minimum R1 bone bound as about 5 ms$^{-1}$, the minimum GM bound as about 2.5 ms$^{-1}$, the maximum GM bound as about 5 ms$^{-1}$, the minimum WM bound as about 1 ms$^{-1}$, the maximum WM bound as about 2.5 ms$^{-1}$, the minimum CSF bound as 0 ms$^{-1}$, and the maximum CSF bound as about 1 ms$^{-1}$.

17. The method of claim 16, wherein calculating at least one MM parameter for each voxel of the plurality of voxels based on a portion of the plurality of MR signals associated with that voxel further comprises calculating at least one additional MRI parameter selected from the group consisting of R2*, $\text{iUTE}_{FA1}$, $\text{iUTE}_{FA2}$, $\text{WATER}_{FA1}$, and $\text{FAT}_{FA1}$.

18. The method of claim 17, wherein assigning the tissue type to each voxel based on at least a portion of the at least one MM parameter associated with that voxel according to the plurality of tissue assignment criteria further comprises:

assigning a tissue type of air to each voxel with a normalized $\text{iUTE}_{FA1}$ value of greater than a minimum air bound;

assigning a tissue type of bone to each voxel with an R2* value of greater than a minimum R2* bone bound;

assigning a tissue type of fat to each voxel with an associated $\text{FAT}_{FA1}$ value greater than a minimum fat bound;

assigning a tissue type of soft tissue to each voxel with an associated $\text{WATER}_{FA1}$ greater than a minimum soft tissue bound; and assigning a tissue type of soft tissue to each voxel not assigned a tissue type according to any preceding tissue assignment criterion of the plurality of tissue assignment criteria.

19. The method of claim 18, wherein assigning the tissue type to each voxel based on at least a portion of the at least one MM parameter associated with that voxel according to the plurality of tissue assignment criteria further comprises defining the minimum air bound as about 0.06, the minimum $R2^*$ bone bound as about 550 $s^{-1}$, the minimum fat bound as about 250, and the minimum soft tissue bound as about 150.

20. The method of claim 13, further comprising assigning a linear attenuation coefficient value $\mu$ to each voxel based on the HU value associated with that voxel.

21. The method of claim 20, wherein assigning the linear attenuation coefficient value $\mu$ to each voxel based on the HU value associated with that voxel further comprises calculating $\mu$ according to a conversion equation of the group of conversion equations consisting of:

$$\mu=(9.6\times10^{-5})\cdot(HU+1000) \text{ cm}^{-1} \text{ for HU}<50; \text{ and}$$

$$\mu=(5.1\times10^{-5})\cdot(HU+1000)+(4.71\times10^{-2}) \text{ cm}^{-1} \text{ for HU}<50.$$

22. The method of claim 13, further comprising assigning a linear attenuation coefficient value to each voxel based on the assigned tissue type and the at least one MRI parameter associated with that voxel.

23. The method of claim 13, further comprising assigning an electron density value to each voxel based on the HU value associated with that voxel.

24. The method of claim 13, further comprising assigning an electron density value to each voxel based on the assigned tissue type and the at least one MM parameter associated with that voxel.

* * * * *